(12) United States Patent
Jung et al.

(10) Patent No.: US 8,793,141 B2
(45) Date of Patent: Jul. 29, 2014

(54) ASSISTANCE RELATED TO HEALTH

(75) Inventors: Edward K. Y. Jung, Bellevue, WA (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1084 days.

(21) Appl. No.: 11/355,517

(22) Filed: Feb. 16, 2006

(65) Prior Publication Data

US 2007/0112595 A1 May 17, 2007

Related U.S. Application Data

(63) Continuation-in-part of application No. 11/283,548, filed on Nov. 17, 2005, and a continuation-in-part of application No. 11/285,753, filed on Nov. 22, 2005, and a continuation-in-part of application No. 11/285,500, filed on Nov. 22, 2005, and a continuation-in-part of application No. 11/314,764, filed on Dec. 21, 2005, now Pat. No. 8,468,029, and a continuation-in-part of application No. 11/314,949, filed on Dec. 21, 2005, and a continuation-in-part of application No. 11/339,316, filed on Jan. 25, 2006, now abandoned.

(51) Int. Cl.
*G06F 19/00* (2011.01)

(52) U.S. Cl.
USPC ............................................................ 705/2

(58) Field of Classification Search
USPC ................ 705/2–4; 600/300–301; 707/104.1; 702/20
See application file for complete search history.

(56) References Cited

U.S. PATENT DOCUMENTS

| | | | |
|---|---|---|---|
| 4,293,845 A | 10/1981 | Villa-Real |
| 4,446,138 A | 5/1984 | Pack |
| 4,838,275 A | 6/1989 | Lee |
| 4,847,764 A | 7/1989 | Halvorson |
| 4,857,716 A | 8/1989 | Gombrich et al. |
| 5,054,493 A | 10/1991 | Cohn et al. |
| 5,279,294 A | 1/1994 | Anderson et al. |
| 5,300,302 A | 4/1994 | Tachon et al. |

(Continued)

FOREIGN PATENT DOCUMENTS

| WO | WO 97/14393 | 4/1997 |
|---|---|---|
| WO | WO 99/45354 | 9/1999 |

(Continued)

OTHER PUBLICATIONS

Cover, Robin, ed.; "Technology Reports: General SGML/XML Applications" [see e.g. "SGML Initiative in Health Care (HL7 Health Level-7 and SGML/XML)"]; Cover pages: Hosted by Oasis; Bearing a date of Nov. 11, 2002, printed on Nov. 16, 2005; pp. 1-95; located at: http://xml.coverpages.org/gen-apps.html.

(Continued)

*Primary Examiner* — John Pauls

(57) ABSTRACT

In one aspect, a method related to health-related data management. In addition to the foregoing, other method and system and program product aspects are described in the claims, drawings, and text forming a part of the present application.

28 Claims, 31 Drawing Sheets

(56) References Cited

U.S. PATENT DOCUMENTS

| | | | |
|---|---|---|---|
| 5,307,263 A | 4/1994 | Brown | |
| 5,495,961 A | 3/1996 | Maestre | |
| 5,537,313 A | 7/1996 | Pirelli | |
| 5,542,420 A | 8/1996 | Goldman et al. | |
| 5,672,154 A | 9/1997 | Sillén et al. | |
| 5,700,998 A | 12/1997 | Palti | |
| 5,710,578 A | 1/1998 | Beauregard et al. | |
| 5,737,539 A | 4/1998 | Edelson et al. | |
| 5,770,226 A | 6/1998 | Hughes, Jr. et al. | |
| 5,940,801 A | 8/1999 | Brown | |
| 5,954,640 A | 9/1999 | Szabo | |
| 5,955,269 A | 9/1999 | Ghai et al. | |
| 5,995,938 A | 11/1999 | Whaley | |
| 6,021,202 A | 2/2000 | Anderson et al. | |
| 6,024,699 A | 2/2000 | Surwit et al. | |
| 6,117,073 A | 9/2000 | Jones et al. | |
| 6,139,494 A | 10/2000 | Cairnes | |
| 6,188,988 B1 | 2/2001 | Barry et al. | |
| 6,209,095 B1 | 3/2001 | Anderson et al. | |
| 6,227,371 B1 | 5/2001 | Song | |
| 6,287,595 B1 | 9/2001 | Loewy et al. | |
| 6,397,190 B1 | 5/2002 | Goetz | |
| 6,421,650 B1 | 7/2002 | Goetz et al. | |
| 6,450,956 B1 | 9/2002 | Rappaport et al. | |
| 6,510,430 B1 | 1/2003 | Oberwager et al. | |
| 6,529,446 B1 | 3/2003 | de la Huerga | |
| 6,609,200 B2 | 8/2003 | Anderson et al. | |
| 6,656,122 B2 | 12/2003 | Davidson et al. | |
| 6,671,818 B1 | 12/2003 | Mikurak | |
| 6,699,193 B2 | 3/2004 | Crutchfield et al. | |
| 6,735,593 B1 | 5/2004 | Williams | |
| 6,764,831 B2 | 7/2004 | Cameron, Sr. et al. | |
| 6,770,029 B2 | 8/2004 | Iliff | |
| 6,790,198 B1 | 9/2004 | White et al. | |
| 6,833,274 B2 | 12/2004 | Lawrence et al. | |
| 6,898,761 B2 | 5/2005 | Johnson | |
| 6,955,873 B1 | 10/2005 | Blum | |
| 7,005,447 B2 | 2/2006 | Ahotupa et al. | |
| 7,016,752 B1 | 3/2006 | Ruben et al. | |
| 7,135,616 B2 | 11/2006 | Heard et al. | |
| 7,136,820 B1 | 11/2006 | Petrus | |
| 7,169,432 B2 | 1/2007 | Tanaka et al. | |
| 7,172,897 B2 | 2/2007 | Blackburn et al. | |
| 7,193,128 B2 | 3/2007 | Copenhaver et al. | |
| 7,197,492 B2 | 3/2007 | Sullivan | |
| 7,216,343 B2 | 5/2007 | Das et al. | |
| 7,280,975 B1 | 10/2007 | Donner | |
| 7,312,243 B1 | 12/2007 | Pravda | |
| 7,351,739 B2 | 4/2008 | Ho et al. | |
| 7,376,585 B2 | 5/2008 | Haller | |
| 7,418,399 B2 | 8/2008 | Schaeffer et al. | |
| 7,454,880 B1 | 11/2008 | Austin et al. | |
| 7,483,839 B2 | 1/2009 | Mayaud | |
| 7,490,085 B2 | 2/2009 | Walker et al. | |
| 7,502,666 B2 | 3/2009 | Siegel et al. | |
| 7,844,609 B2 | 11/2010 | Kenedy et al. | |
| 2001/0037340 A1* | 11/2001 | Hawkins et al. | 707/104.1 |
| 2001/0039503 A1 | 11/2001 | Chan et al. | |
| 2002/0023172 A1 | 2/2002 | Gendron et al. | |
| 2002/0027164 A1 | 3/2002 | Mault et al. | |
| 2002/0032580 A1 | 3/2002 | Hopkins | |
| 2002/0032583 A1 | 3/2002 | Joao | |
| 2002/0033753 A1 | 3/2002 | Imbo | |
| 2002/0047867 A1 | 4/2002 | Mault et al. | |
| 2002/0049738 A1 | 4/2002 | Epstein | |
| 2002/0065682 A1 | 5/2002 | Goldenberg | |
| 2002/0091546 A1 | 7/2002 | Christakis et al. | |
| 2002/0099686 A1 | 7/2002 | Schwartz et al. | |
| 2002/0106429 A1 | 8/2002 | Mudar et al. | |
| 2002/0111932 A1 | 8/2002 | Roberge et al. | |
| 2002/0116225 A1 | 8/2002 | Morse et al. | |
| 2002/0128259 A1 | 9/2002 | Ghazzi et al. | |
| 2002/0147317 A1 | 10/2002 | Bentsen et al. | |
| 2002/0156651 A1 | 10/2002 | Florio et al. | |
| 2002/0192310 A1 | 12/2002 | Bland et al. | |
| 2002/0194221 A1 | 12/2002 | Strong et al. | |
| 2003/0004403 A1 | 1/2003 | Drinan et al. | |
| 2003/0028399 A1 | 2/2003 | Davis et al. | |
| 2003/0036683 A1 | 2/2003 | Kehr et al. | |
| 2003/0046114 A1 | 3/2003 | Davies et al. | |
| 2003/0069757 A1 | 4/2003 | Greenberg | |
| 2003/0072770 A1 | 4/2003 | McAnalley et al. | |
| 2003/0082544 A1 | 5/2003 | Fors et al. | |
| 2003/0086338 A1 | 5/2003 | Sastry et al. | |
| 2003/0099158 A1 | 5/2003 | De la Huerga | |
| 2003/0114475 A1 | 6/2003 | Fox et al. | |
| 2003/0135388 A1 | 7/2003 | Martucci et al. | |
| 2003/0137067 A1 | 7/2003 | Cooper et al. | |
| 2003/0139655 A1 | 7/2003 | Dodds | |
| 2003/0158756 A1 | 8/2003 | Abramson | |
| 2003/0163353 A1 | 8/2003 | Luce et al. | |
| 2003/0186001 A1 | 10/2003 | Khan | |
| 2003/0194350 A1 | 10/2003 | Stamatelos et al. | |
| 2003/0204412 A1 | 10/2003 | Brier | |
| 2003/0208381 A1 | 11/2003 | Walter et al. | |
| 2003/0229455 A1 | 12/2003 | Bevilacqua et al. | |
| 2003/0233124 A1 | 12/2003 | Hara et al. | |
| 2003/0233250 A1 | 12/2003 | Joffe et al. | |
| 2004/0006491 A1 | 1/2004 | Brown et al. | |
| 2004/0039599 A1 | 2/2004 | Fralic | |
| 2004/0064342 A1 | 4/2004 | Browne et al. | |
| 2004/0078220 A1 | 4/2004 | Jackson | |
| 2004/0088187 A1 | 5/2004 | Chudy et al. | |
| 2004/0088374 A1 | 5/2004 | Webb et al. | |
| 2004/0111298 A1 | 6/2004 | Schoenberg | |
| 2004/0116780 A1 | 6/2004 | Brown | |
| 2004/0121767 A1 | 6/2004 | Simpson et al. | |
| 2004/0122661 A1 | 6/2004 | Hawkinson et al. | |
| 2004/0122707 A1 | 6/2004 | Sabol et al. | |
| 2004/0122790 A1 | 6/2004 | Walker et al. | |
| 2004/0138926 A1 | 7/2004 | Ishikawa et al. | |
| 2004/0143403 A1 | 7/2004 | Brandon et al. | |
| 2004/0146592 A1 | 7/2004 | Garrity et al. | |
| 2004/0176984 A1 | 9/2004 | White et al. | |
| 2004/0215486 A1 | 10/2004 | Braverman | |
| 2004/0221855 A1 | 11/2004 | Ashton | |
| 2004/0243437 A1 | 12/2004 | Grace et al. | |
| 2004/0243441 A1 | 12/2004 | Bocionek et al. | |
| 2004/0254868 A1* | 12/2004 | Kirkland et al. | 705/35 |
| 2005/0027570 A1 | 2/2005 | Maier et al. | |
| 2005/0033121 A1 | 2/2005 | Modrovich | |
| 2005/0033773 A1 | 2/2005 | Roberge et al. | |
| 2005/0038558 A1 | 2/2005 | Keene | |
| 2005/0038674 A1 | 2/2005 | Braig et al. | |
| 2005/0061336 A1 | 3/2005 | Goetz et al. | |
| 2005/0070607 A1 | 3/2005 | Andrus et al. | |
| 2005/0075794 A1* | 4/2005 | Hoffman et al. | 702/20 |
| 2005/0090718 A1 | 4/2005 | Dodds | |
| 2005/0101841 A9 | 5/2005 | Kaylor et al. | |
| 2005/0102159 A1 | 5/2005 | Mondshine | |
| 2005/0118202 A1 | 6/2005 | Yamashita et al. | |
| 2005/0147667 A1 | 7/2005 | Rines | |
| 2005/0149354 A1 | 7/2005 | Cyr et al. | |
| 2005/0180962 A1 | 8/2005 | Raz et al. | |
| 2005/0182653 A1 | 8/2005 | Urban et al. | |
| 2005/0191716 A1 | 9/2005 | Surwit et al. | |
| 2005/0192487 A1 | 9/2005 | Cosentino et al. | |
| 2005/0211768 A1 | 9/2005 | Stillman | |
| 2005/0216313 A1 | 9/2005 | Claud et al. | |
| 2005/0216390 A1 | 9/2005 | Snider et al. | |
| 2005/0256745 A1 | 11/2005 | Dalton | |
| 2005/0260610 A1* | 11/2005 | Kurtz et al. | 435/6 |
| 2005/0260679 A1 | 11/2005 | Kellerman et al. | |
| 2005/0261255 A1 | 11/2005 | Serhan et al. | |
| 2005/0267356 A1 | 12/2005 | Ramasubramanian et al. | |
| 2005/0271596 A1 | 12/2005 | Friedman et al. | |
| 2006/0047538 A1 | 3/2006 | Condurso et al. | |
| 2006/0064250 A1 | 3/2006 | Goldstein | |
| 2006/0089542 A1 | 4/2006 | Sands | |
| 2006/0090765 A1 | 5/2006 | Surina | |
| 2006/0111944 A1 | 5/2006 | Sirmans et al. | |
| 2006/0129324 A1 | 6/2006 | Rabinoff et al. | |
| 2006/0136259 A1 | 6/2006 | Weiner et al. | |
| 2006/0161443 A1 | 7/2006 | Rollins | |

(56) References Cited

U.S. PATENT DOCUMENTS

| | | | |
|---|---|---|---|
| 2006/0177637 | A1 | 8/2006 | Kimura |
| 2006/0248468 | A1 | 11/2006 | Constantine et al. |
| 2006/0254580 | A1 | 11/2006 | Chalmers et al. |
| 2006/0260679 | A1 | 11/2006 | Aratani et al. |
| 2006/0287891 | A1* | 12/2006 | Grasso et al. ............ 705/3 |
| 2007/0018810 | A1 | 1/2007 | Smythe et al. |
| 2007/0035403 | A1* | 2/2007 | Krishna et al. ............ 340/573.1 |
| 2007/0065506 | A1 | 3/2007 | Kelly et al. |
| 2007/0067186 | A1 | 3/2007 | Brenner et al. |
| 2007/0068959 | A1 | 3/2007 | D'Silva |
| 2007/0087048 | A1 | 4/2007 | Abrams et al. |
| 2007/0093448 | A1 | 4/2007 | Westermann et al. |
| 2007/0136092 | A1 | 6/2007 | Jung et al. |
| 2007/0161076 | A1 | 7/2007 | Halden |
| 2007/0192134 | A1 | 8/2007 | Littenberg et al. |
| 2008/0097784 | A1 | 4/2008 | Miller et al. |
| 2008/0139907 | A1 | 6/2008 | Rao et al. |
| 2008/0299013 | A1 | 12/2008 | Trieu et al. |
| 2010/0081144 | A1 | 4/2010 | Holmes et al. |

FOREIGN PATENT DOCUMENTS

| | | |
|---|---|---|
| WO | WO 00/60362 | 10/2000 |
| WO | WO 01/79529 A1 | 10/2001 |
| WO | WO 2004/082359 A2 | 9/2004 |
| WO | WO 2005/018632 A1 | 3/2005 |
| WO | WO 2005/062849 A2 | 7/2005 |
| WO | WO 2007/061838 A2 | 5/2007 |

OTHER PUBLICATIONS

Goedert, Joseph, ed.; "XML Comes of Age for Data Exchange"; Health Data Management; Bearing dates of Nov. 16, 2005 and 2005, printed on Nov. 16, 2005; pp. 1-4; SourceMedia, Inc; located at: http://www.healthdatamanagement.com/html/current/CurrentIssueStory.cfm?PostID=16205.

Guo, Jinqiu; Araki, Kenji; Tanaka, Koji; Sato, Junzo; Suzuki, Muneou; Takada, Akira; Suzuki, Toshiaki; Nakashima, Yusei; Yoshihara, Hiroyuki; "The Latest MML (Medical Markup Language) Version 2.3—XML-Based Standard for Medical Data Exchange/Storage"; Journal of Medical Systems; Bearing dates of Aug. 2003 and 2003; printed on Nov. 16, 2005; pp. 357-366; vol. 27, No. 4; Plenum Publishing Corporation; located at: http://lob.kuhp.kyoto-u.acjp/paper/200308mm123JMS/mml23JMS.pdf.

Kahn Jr., Charles E.; De La Cruz, Norberto B.; "Extensible Markup Language (XML) in Health Care: Integration of Structured Reporting and Decision Support"; Office of Clinical Informatics; printed on Nov. 16, 2005; pp. 1-5; located at: http://www.amia.org/pubs/symposia/D004673.PDF.

McDonald, Carol; Srinivas, Raghavan N.; "How Java Technology and XML Are Improving Healthcare in Brazil"; Java.sun.com; Bearing dates of Feb. 2004 and 1994-2005, printed on Nov. 16, 2005; pp. 1-9; Sun Microsystems, Inc.; located at: http://java.sun.com/developer/technicalArticles/xml/brazil/index.html.

U.S. Appl. No. 11/314,945, Jung et al.

U.S. Appl. No. 11/291,532, Jung et al.

U.S. Appl. No. 11/291,482, Jung et al.

PCT International Search Report; International App. No. PCT/ US 06/44278; 2 pages; Aug. 17, 2007.

PCT International Search Report; International App. No. PCT/ US 06/44269; 2 pages; Sep. 18, 2007.

PCT International Search Report; International App. No. PCT/US 06/44664; Apr. 14, 2008; pp. 1-3.

PCT International Search Report; International App. No. PCT/US07/25379; May 13, 2008; pp. 1-2.

PCT International Search Report; International App. No. PCT/US07/25417; May 14, 2008; pp. 1-3.

PCT International Search Report; International App. No. PCT/US07/25417; May 19, 2008; pp. 1-2.

PCT International Search Report; International App. No. PCT/US2007/025450; May 23, 2008; pp. 1-2.

PCT International Search Report; International App. No. PCT/US06/47835; Jul. 14, 2008; pp. 1-2.

Smith, Stevie; "New Chip Identifies Bird Flu in Humans"; The Tech Herald.com, WOTR Limited; 2008; located at: www.thetechherald.com/article/php200813/520/new-chin-identifies-bird-flu-in-humans; Bearing a date of Mar. 25, 2008; printed on Sep. 8, 2008; pp. 1-6.

PCT International Search Report; International App. No. PCT/US2007/025451; Sep. 15, 2008; pp. 1-2.

PCT International Search Report; International App. No. PCT/US07/20272; Sep. 15, 2008; pp. 1-2.

PCT International Search Report; International App. No. PCT/US07/20305; Sep. 11, 2008; pp. 1-2.

PCT International Search Report; International App. No. PCT/US07/20283; Sep. 11, 2008; pp. 1-2.

PCT International Search Report; International App. No. PCT/US07/14994; Sep. 9, 2008; pp. 1-2.

PCT International Search Report; International App. No. PCT/US2008/007993; Sep. 8, 2008; pp. 1-3.

PCT International Search Report; International App. No. PCT/US06/47451; Sep. 5, 2008; pp. 1-2.

PCT International Search Report; International App. No. PCT/US06/44658; Aug. 29, 2008; pp. 1-2.

PCT International Search Report; International App. No. PCT/US06/44279; Aug. 19, 2008; pp. 1-3.

PCT International Search Report; International App. No. PCT/US06/44283; Aug. 18, 2008; pp. 1-2.

PCT International Search Report; International App. No. PCT/US07/14266; Jul. 21, 2008; pp. 1-2.

UK Intellectual Property Office Examination Report Under Section 18(3); App. No. GB1000316.8; Jul. 26, 2011; pp. 1-3.

U.S. Appl. No. 13/371,765, Jung et al.

"Microsoft Press Computer Dictionary: The Comprehensive Standard for Business, School, Library, and Home"; bearing a date of Nov. 1, 1993; 1 page; Edition 2; Microsoft Press; IBSN: 9781556155970 (whole book not provided).

Roberts et al.; "Nutraceuticals: The Complete Encyclopedia of Supplements, Herbs, Vitamins and Healing Foods"; American Nutraceutical Association; bearing a date of Jan. 1, 2001; pp. 1-3 (669 pages, not provided); Perigee Trade; IBSN: 0399526323 (whole book not provided).

Mullett, Charles J. et al.; "Computerized antimicrobial decision support: an offline evaluation of a database-driven empiric antimicrobial guidance program in hospitalized patients with a bloodstream infection"; International Journal of Medical Informatics; 2004; pp. 455-460; vol. 73; Elsevier Ireland Ltd.

Sriskanthan, N. and Subramanian, K. R.; "Braille Display Terminal for Personal Computers"; IEEE Transactions on Consumer Electronics; May 1990; pp. 121-128; vol. 36, No. 2; IEEE.

Walt et al.; "Biological Warfare, A Host of Detection Strategies Have Been Developed, But Each Has Significant Limitations"; Analytical Chemistry; bearing a date of Dec. 1, 2000; pp. 738A-747A.

Krishna et al.; "Glutathione and γ-glutamyl transpeptidase are differentially distributed in the olfactory mucosa of rats"; Cell Tissue Res; bearing a date of Jul. 1992; pp. 475-484; vol. 270; Springer-Verlag.

"Component"; IEEE Xplore Digital Library; printed on Oct. 3, 2013; 1 page; IEEE; located at: http://eeexplore.ieee.org/xpls/dictionary.jsp?stdDiet=match_keyword&def_term=component.

* cited by examiner

FIG. 13A

| 13A | 13B | 13C | 13D |

Key To FIG. 13

1200 — providing and/or receiving health regimen information using one or more filtering parameters

1300 providing and/or receiving health regimen information using one or more filtering parameters concerning heredity information about an end-user of the health regimen information

1302 providing and/or receiving health regimen information using one or more filtering parameters concerning heredity information about one or more family members of an end-user of the health regimen information

1304 providing and/or receiving health regimen information using one or more filtering parameters concerning genetic profile information about an end-user of the health regimen information

1306 providing and/or receiving health regimen information using one or more filtering parameters concerning genetic profile information about one or more family members of an end-user of the health regimen information

1308 providing and/or receiving health regimen information using one or more filtering parameters concerning inferred genetic signature information derived from genetic signature information about one or more family members of an end-user of the health regimen information (A)

(B)

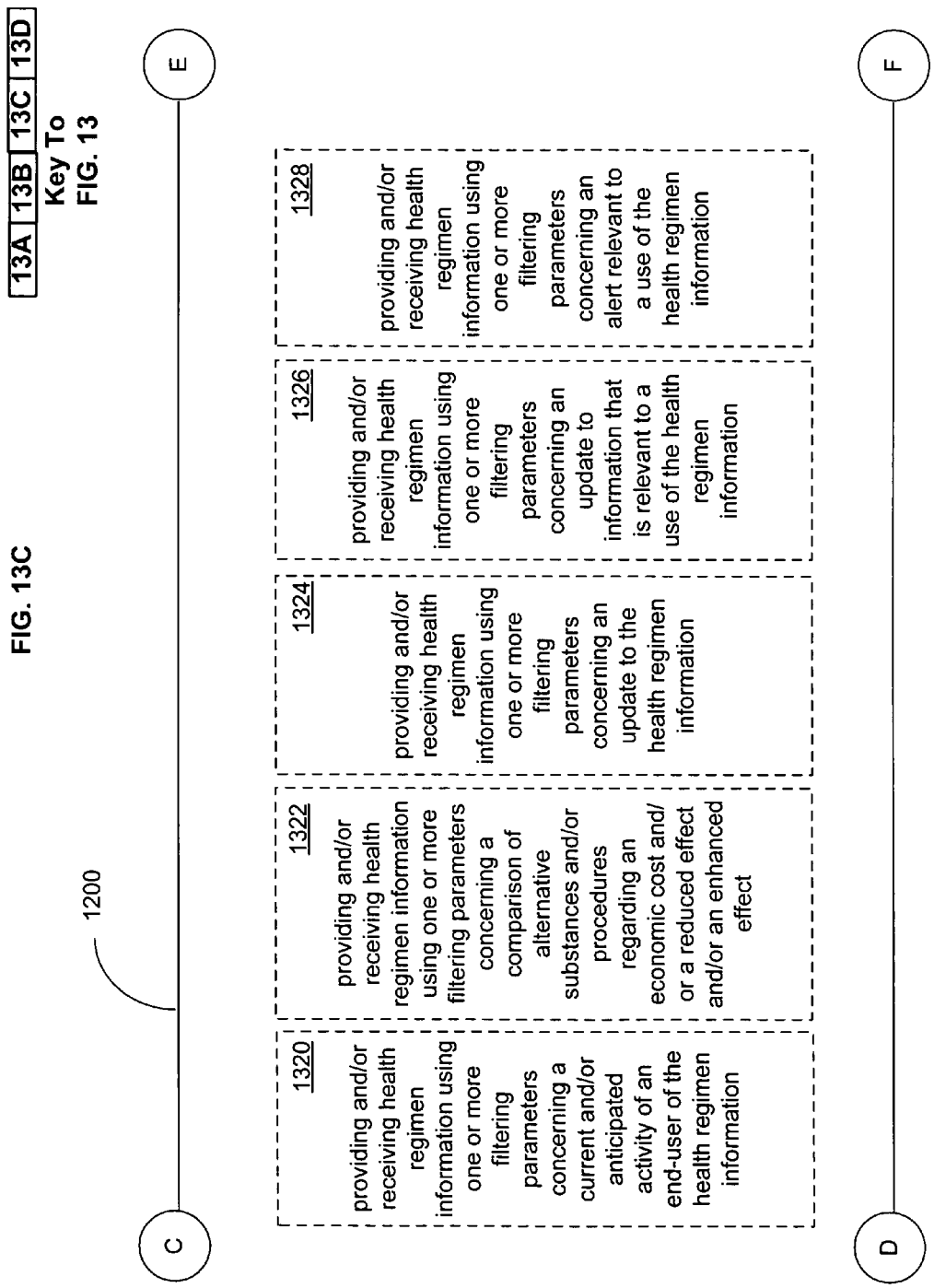

FIG. 13D

| 13A | 13B | 13C | 13D |

Key To
FIG. 13

1330 providing and/or receiving health regimen information using one or more filtering parameters concerning credibility information relevant to a use of the health regimen information

1332 providing and/or receiving health regimen information using one or more filtering parameters concerning a reference to information relevant to a use of the health regimen information

1334 providing and/or receiving health regimen information using one or more filtering parameters concerning a variation of the health regimen information

1336 providing and/or receiving health regimen information using one or more filtering parameters concerning a medical condition of an end-user of the health regimen information

1338 providing and/or receiving health regimen information using one or more filtering parameters concerning a condition external to an end-user of the health regimen information

1340 providing and/or receiving health regimen information using one or more filtering parameters concerning information about a physiological process of an end-user of the health regimen information

1200

E

F

ASSISTANCE RELATED TO HEALTH

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. Stephen G. Kunin, Benefit of Prior-Filed Application, USPTO Electronic Official Gazette, Mar. 18, 2003 at http://www.uspto.gov/web/offices/com/sol/og/2003/week11/pat-bene.htm. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

RELATED APPLICATIONS

1. For purposes of the USPTO extra-statutory requirements, the present application constitutes a continuation in part of currently co-pending United States patent application entitled Providing Assistance Related to Health, naming Edward K. Y. Jung, Royce A. Levien, Robert W. Lord, Mark A. Malamud, John D. Rinaldo, Jr., and Lowell L. Wood, Jr., as inventors, U.S. application Ser. No. 11/283,548, filed Nov. 17, 2005.
2. For purposes of the USPTO extra-statutory requirements, the present application constitutes a continuation in part of currently co-pending United States patent application entitled User Interface for Providing Assistance Related to Health, naming Edward K.Y. Jung, Royce A. Levien, Robert W. Lord, Mark A. Malamud, John D. Rinaldo, Jr., and Lowell L. Wood, Jr., as inventors, U.S application Ser. No. 11/285,753, filed Nov. 22, 2005.
3. For purposes of the USPTO extra-statutory requirements, the present application constitutes a continuation in part of currently co-pending United States patent application entitled User Interface for Providing Assistance Related to Health, naming Edward K.Y. Jung, Royce A. Levien, Robert W. Lord, Mark A. Malamud, John D. Rinaldo, Jr., and Lowell L. Wood, Jr., as inventors, U.S. application Ser. No. 11/285,500, filed Nov. 22, 2005.
4. For purposes of the USPTO extra-statutory requirements, the present application constitutes a continuation in part of currently co-pending United States patent application entitled Subscriptions for Providing Assistance Related to Health, naming Edward K. Y. Jung, Royce A. Levien, Robert W. Lord, Mark A. Malamud, John D. Rinaldo, Jr., and Lowell L. Wood, Jr., as inventors, U.S. application Ser. No. 11/314,764, filed Dec. 21, 2005 now U.S. Pat. No. 8,468,029.
5. For purposes of the USPTO extra-statutory requirements, the present application constitutes a continuation in part of currently co-pending United States patent application entitled Research in Providing Assistance Related to Health, naming Edward K. Y. Jung, Royce A. Levien, Robert W. Lord, Mark A. Malamud, John D. Rinaldo, Jr., and Lowell L. Wood, Jr., as inventors, U.S. application Ser. No. 11/314,949 filed Dec. 21, 2005.
6. For purposes of the USPTO extra-statutory requirements, the present application constitutes a continuation in part of currently co-pending United States patent application entitled Payments in Providing Assistance Related to Health, naming Edward K. Y. Jung, Royce A. Levien, Robert W. Lord, Mark A. Malamud, John D. Rinaldo, Jr., and Lowell L. Wood, Jr., as inventors, U.S. application Ser. No. 11/339,316 filed Jan. 25, 2006 now abandoned.

TECHNICAL FIELD

The present application relates, in general, to health-related data management.

SUMMARY

In one aspect, a method related to health-related data management includes but is not limited to providing and/or receiving health regimen information using one or more filtering parameters. In addition to the foregoing, other method aspects are described in the claims, drawings, and text forming a part of the present application.

In one aspect, a system related to health-related data management includes but is not limited to circuitry for providing and/or receiving health regimen information using one or more filtering parameters. In addition to the foregoing, other system aspects are described in the claims, drawings, and text forming a part of the present application.

In one or more various aspects, related systems include but are not limited to circuitry and/or programming and/or electromechanical devices and/or optical devices for effecting the herein-referenced method aspects; the circuitry and/or programming and/or electromechanical devices and/or optical devices can be virtually any combination of hardware, software, and/or firmware configured to effect the herein-referenced method aspects depending upon the design choices of the system designer skilled in the art.

In one aspect, a program product includes but is not limited to a signal bearing medium bearing one or more instructions for providing and/or receiving health regimen information using one or more filtering parameters. In addition to the foregoing, other program product aspects are described in the claims, drawings, and text forming a part of the present application.

In addition to the foregoing, various other method, system, and/or program product aspects are set forth and described in the teachings such as the text (e.g., claims and/or detailed description) and/or drawings of the present application.

The foregoing is a summary and thus contains, by necessity, simplifications, generalizations and omissions of detail;

consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

The use of the same symbols in different drawings typically indicates similar or identical items.

DETAILED DESCRIPTION

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

Figure 1:
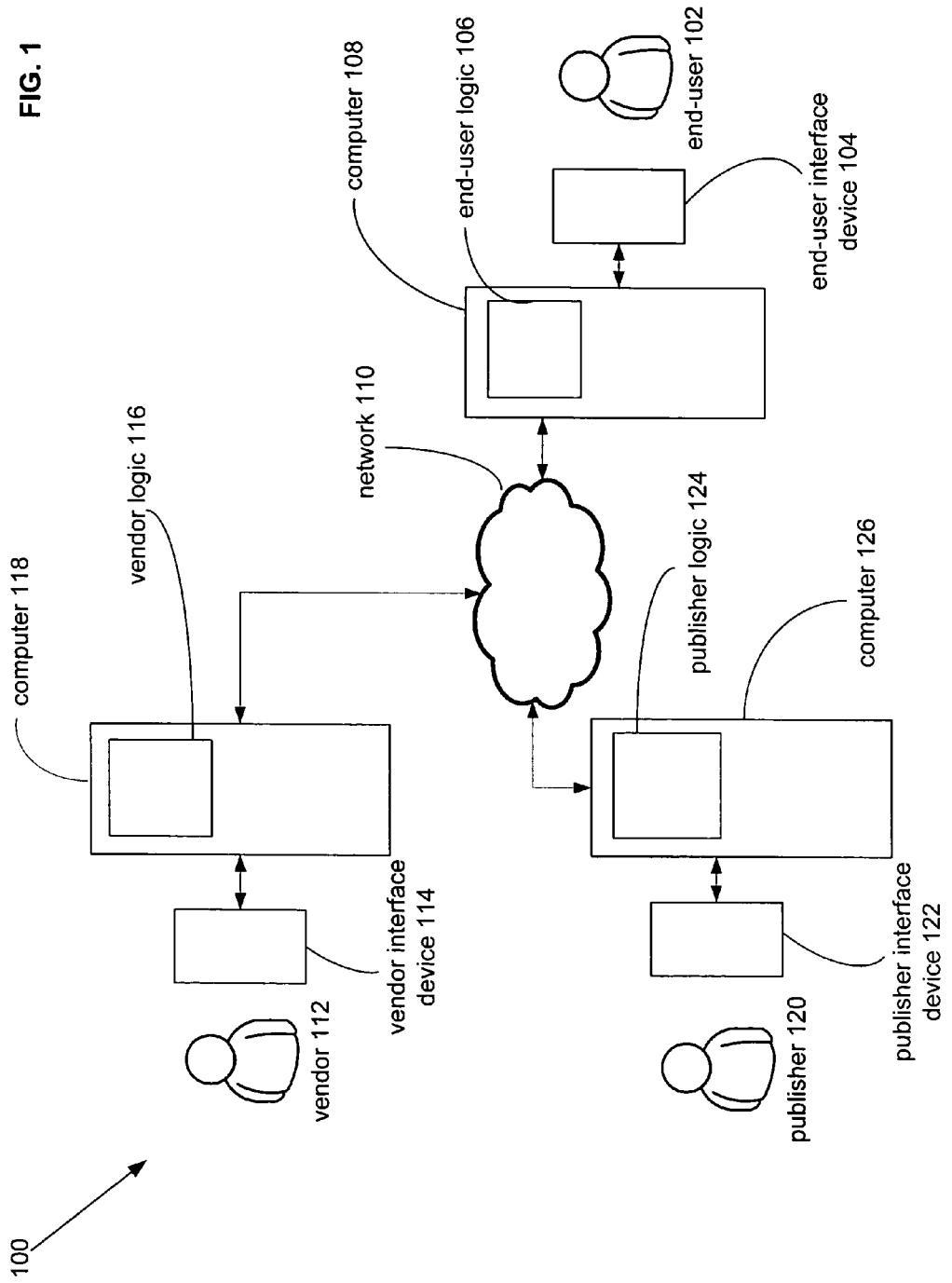
FIG. 1 depicts one implementation of an exemplary environment in which the methods and systems described herein may be represented.

FIG. 1 illustrates an exemplary environment 100 in which embodiments may be used. The end-user 102 may be a person who wishes to access information regarding pharmaceutical, nutraceutical, veterinary, dietary, and/or nutritional substances, procedures, processes, and/or practices of interest for use in a health regimen or regimens. The end-user interface device 104 may be a keyboard, mouse, trackball, monitor, microphone and speakers, and/or other interface device or devices for a human to interface with the end-user logic 106 of computer 108. The end-user logic 106 may include at least a portion of the hardware/software/firmware of the computer 108. The computer 108 may be used by the end-user 102 to access such information via another computer or computers represented by the network 110.

Vendor 112 may be a person and/or persons and/or entity and/or entities that may supply pharmaceutical, nutraceutical, veterinary, dietary, and/or nutritional substances, procedures, processes, and/or practices of interest for use in a health regimen or regimens. The vendor interface device 114 may be a keyboard, mouse, trackball, monitor, microphone and speakers, and/or other interface device or devices for a human to interface with the vendor logic 116 of computer 118. The vendor logic 116 may include at least a portion of the hardware/software/firmware of the computer 118. The vendor 112 may use the computer 118 to provide information and channels, making the vendor 112 available to provide pharmaceutical, nutraceutical, veterinary, dietary, and/or nutritional substance, procedure, processes, and/or practices of interest, via another computer or computers represented by the network 110, to, among others, the end-user 102.

Publisher 120 may be a person and/or persons and/or entity and/or entities that may supply information about pharmaceutical, nutraceutical, veterinary, dietary, and/or nutritional substances procedures, processes, and/or practices of interest for use in a health regimen or regimens, and/or about authorities having expertise or claimed expertise regarding pharmaceutical, nutraceutical, veterinary, dietary, and/or nutritional substances procedures, processes, and/or practices of interest for use in a health regimen or regimens. The publisher interface device 122 may be a keyboard, mouse, trackball, monitor, microphone and speakers, and/or other interface device or devices for a human to interface with the publisher logic 124 of computer 126. The publisher logic 124 may include at least a portion of the hardware/software/firmware of the computer 126. The publisher 120 may use the computer 126 to provide such information about pharmaceutical, nutraceutical, veterinary, dietary, and/or nutritional substance, procedure, processes, and/or practices of interest for use in a health regimen or regimens, via another computer or computers represented by the network 110, to, among others, the end-user 102. The publisher 120 represents a wide variety of information providers, including but not limited to magazine publishers, book publishers, website maintainers, weblog proprietors, experts, research organizations, and users of the pharmaceutical, nutraceutical, veterinary, dietary, and/or nutritional substances procedures, processes, and/or practices of interest for use in a health regimen or regimens.

End-users 102, vendors 112, and publishers 120 are not necessarily mutually exclusive categories. One person, group of persons, entity, or group of entities may be categorized as an end-user 102, vendor 112, and/or publisher 120 simultaneously or at different times. End-users 102, vendors 112, and publishers 120 are exemplary parties and do not represent all users. Exemplary descriptions including the end-user 102 are not limiting and do not preclude use of an embodiment by vendors 112 and/or publishers 120.

Figure 2:
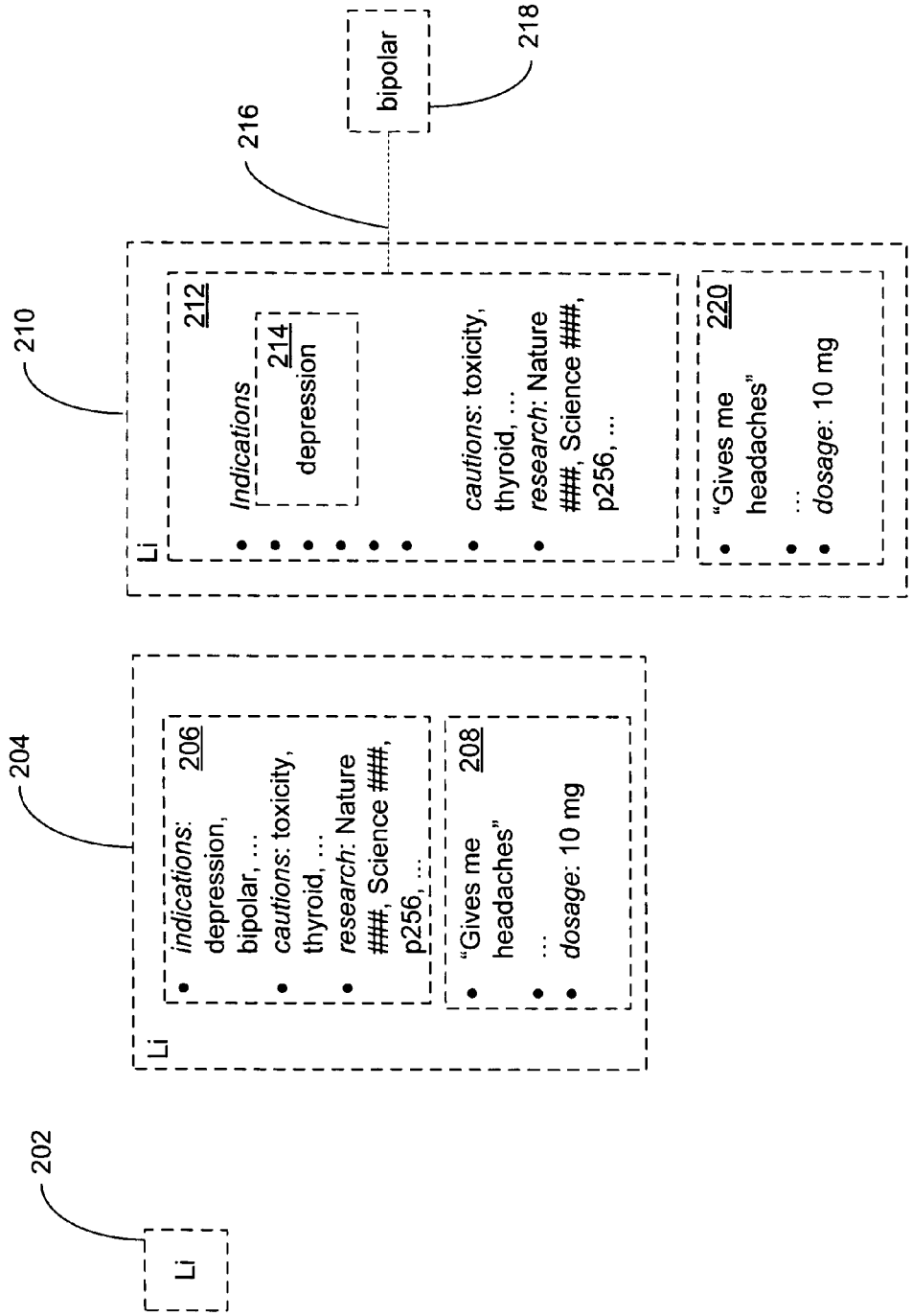
FIG. 2 depicts alternative exemplary embodiments.

FIG. 2 depicts alternative exemplary embodiments of a data entity, including depiction of alternative exemplary embodiments of health regimen data entities associated with some amount of additional information. This additional information may include but is not limited to an item of associative information, e.g., a linkage or a resolvable reference, to one or more other health regimen data entities in the data structure/data structures (e.g., which may be distributed data structures), e.g., a pointer, identifier, and/or a link. In FIG. 2 and the other figures, items of associative data are depicted by lines and/or arrows between health regimen data entities, or are implicit of the relationship between a nesting health regimen data entity and any health regimen data entity nested within or at any depth; such implicit items of associative data are shown by the illustrated nesting. The additional information may also include but is not limited to substantive information, e.g., where the health regimen data entity includes the identity of a substance and the additional information describes a potential use or specifies a dosage. Here health regimen data entity 202 includes an identifier for the element lithium (Li). The health regimen data entity 204 illustrates an alternative exemplary embodiment of the health regimen data entity 202. The end-user 102 may select the health regimen data entity 202 to access additional information that is included in association with the health regimen data entity 202. The additional information may be organized in some defined way, as illustrated in organizational structure 206, or unorganized as in collection 208. The health regimen data entity 210 shows another alternative exemplary embodiment of the health regimen data entity 202. Here the additional information is illustrated as being included in an organizational structure 212. One of the items of additional information associated with the organizational structure 212 is depicted as another health regimen data entity 214 "nested" within health regimen data entity 212. Another of the items of additional information associated with the health regimen data entity 212 is linked by an item of associative information 216 to another health regimen data entity 218. Organizational principles such as those illustrated by the relationship between health regimen data entity 212 and health regimen data entity 214, and by the relationship between health regimen data entity 212, item of associative information 216, and health regimen data entity 218, may be replicated at any level of an organizational structure, or in an unorganized collection such as collection 220. It is to be understood that in substantially all examples referring to "an identifier for lithium" herein, analogous examples utilizing the alternatives such as those from FIG. 2, will be recognized by those of skill in the art. Such examples are not expressly set forth herein for the sake of clarity.

The additional information discussed in the immediately previous paragraph may include, or may be included in, one or more characterization tags associated with one or more health regimen data entities. Further, a characterization tag may include, or may be included in, one or more health regimen data entities.

Figure 3:
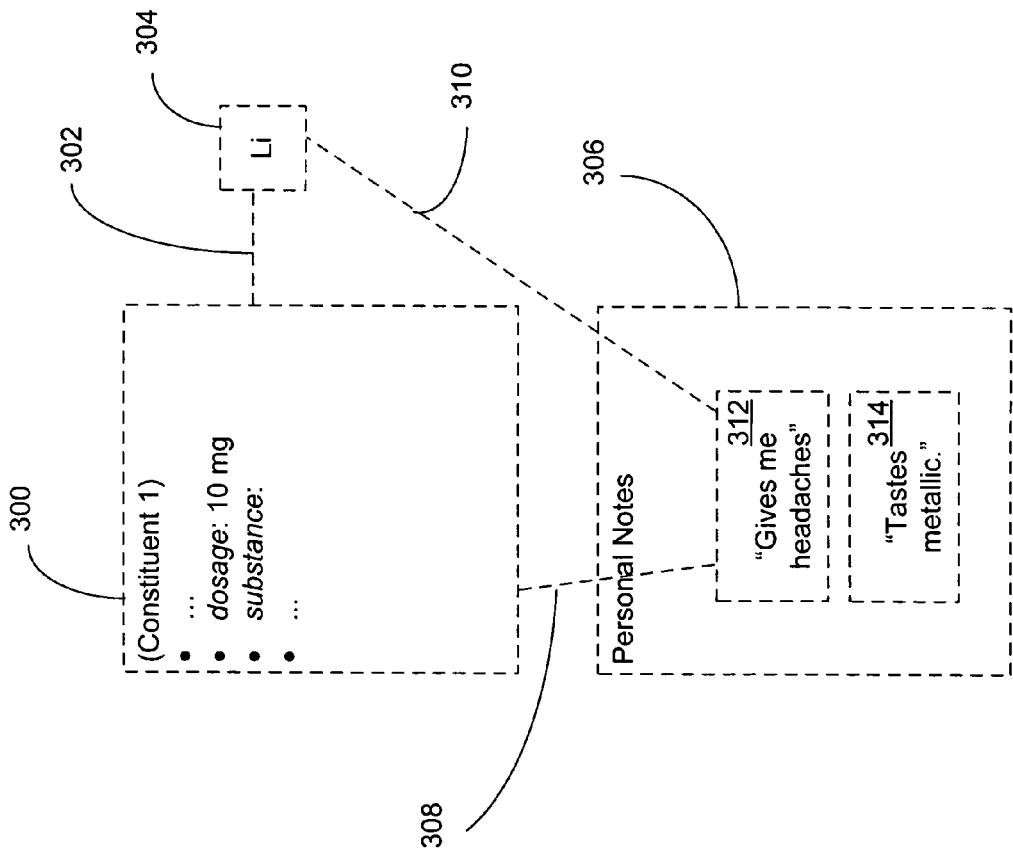
FIG. 3 illustrates alternative exemplary embodiments.

FIG. 3 illustrates an alternative exemplary embodiment of a health regimen data entity. Depicted is nesting health regimen data entity 300, which includes additional information relevant in the context of the nesting health regimen data entity 300, here, "constituent 1." The identity of constituent 1 is not nested within nesting health regimen data entity, but an item of associative data 302 links to a health regimen data entity 304 identifying lithium ("Li"). Also illustrated is a health regimen data entity 306 having additional information detailing personal notes from users of constituent 1. Shown are nested health regimen data entities 312 and 314. The health regimen data entity 312 is linked to the nesting health regimen data entity 300 by an item of associative data 308 and to the health regimen data entity 304 by an item of associative data 310.

Figure 4:
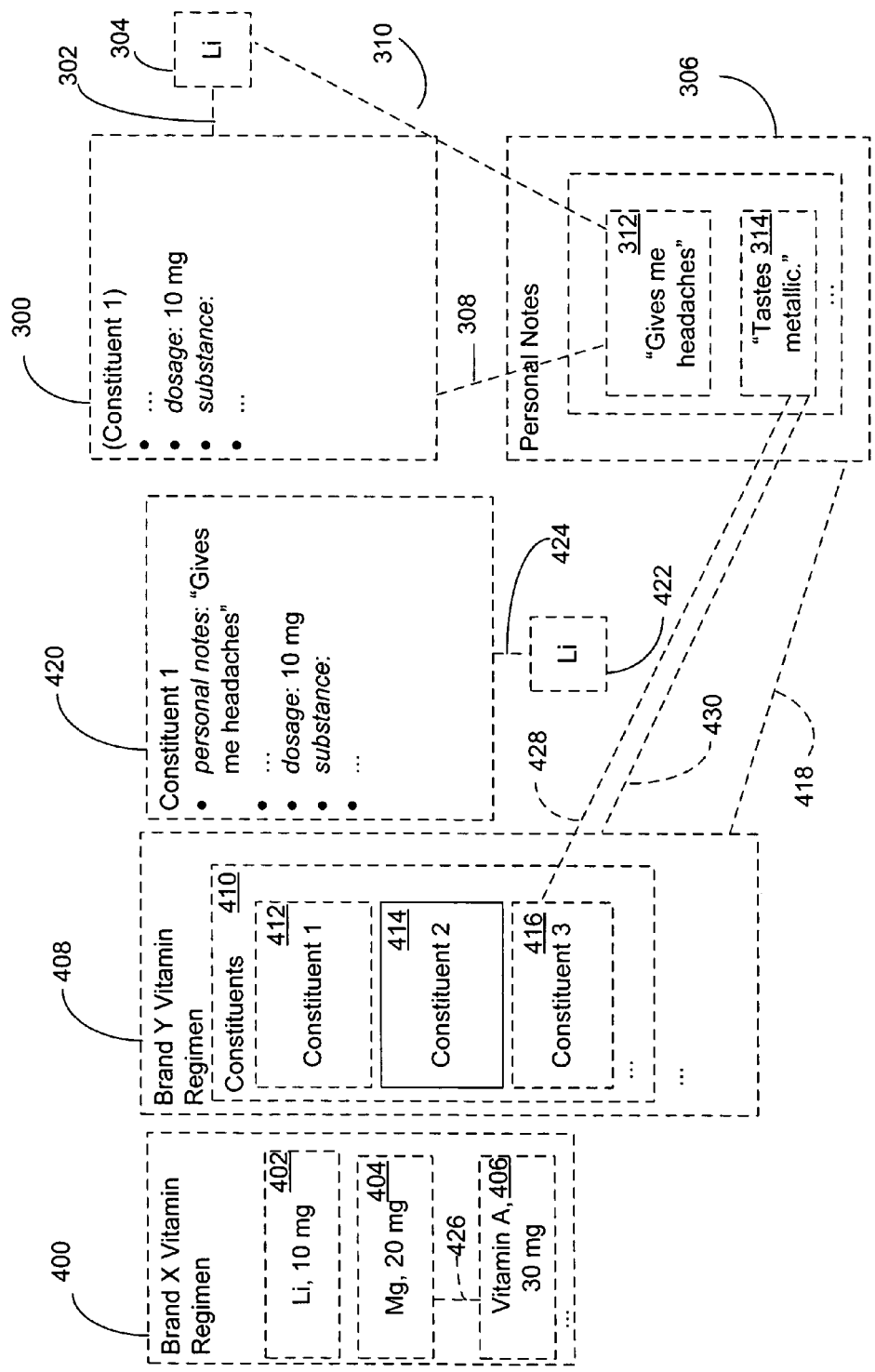
FIG. 4 illustrates alternative exemplary embodiments.

FIG. 4 illustrates a number of alternative exemplary health regimen data entities organized in the data structure according to different organizational schemes. Shown is nesting health regimen data entity 400, including three nested health regimen data entities 402, 404, and 406, for three components of a "Brand X" vitamin regimen. Depicted is nesting health regimen data entity 408, including a nested and nesting health regimen data entity 410. Nested and nesting health regimen data entity 410 includes nested health regimen data entities 412, 414, and 416, components of a "Brand Y" vitamin regimen. Illustrated is nesting health regimen data entity 408 associated with health regimen data entity 306 with an item of associative data 418, linking the personal notes of health regimen data entity 306 with the "Brand Y" vitamin regimen of nesting health regimen data entity 408. Illustrated is health regimen data entity 420, pertaining to "constituent 1," including additional information about personal notes, dosage, and substances. The health regimen data entity 420 is shown linked to health regimen data entity 422, identifying Lithium, by an item of associative data 424. The health regimen data entity 406 is shown linked to another health regimen data entity 404 by an item of associative data 426. The health regimen data entity 314 is shown linked to the health regimen data entity 416 by an item of associative data 428. The health regimen data entity 314 is also shown linked to health regimen data entity 408 by an item of associative data 430.

The nesting as illustrated in FIGS. 2, 3, and 4 is accomplished with items of associative information that are associated with either the nesting health regimen data entity or with one or more of the illustrated nested health regimen data entities. The nesting health regimen data entity might represent, e.g., the name of a vitamin supplement, and the nested health regimen data entities might represent, e.g., five constituent supplements comprised by the named vitamin supplement. In another example, the nesting health regimen data entities might represent identifiers of taxonomic classifications to which the constituent belongs, such as chemical classes (such as water soluble or fat soluble vitamins), classes of effect or action (such as beta-blockers, neurotransmitters, or strength enhancers).

A health regimen data entity may be associated with another health regimen data entity in a variety of ways. The first health regimen data entity may be associated with the second health regimen data entity with an item of associative information associated with one or the other or both. The first health regimen data entity may be associated with the second health regimen data entity as well as with additional health regimen data entities simultaneously. The multiply-referenced health regimen data entity may actually be multiple health regimen data entities in the data structure, or it may be a single health regimen data entity with multiple items of associative information used to reference it.

Figure 5:
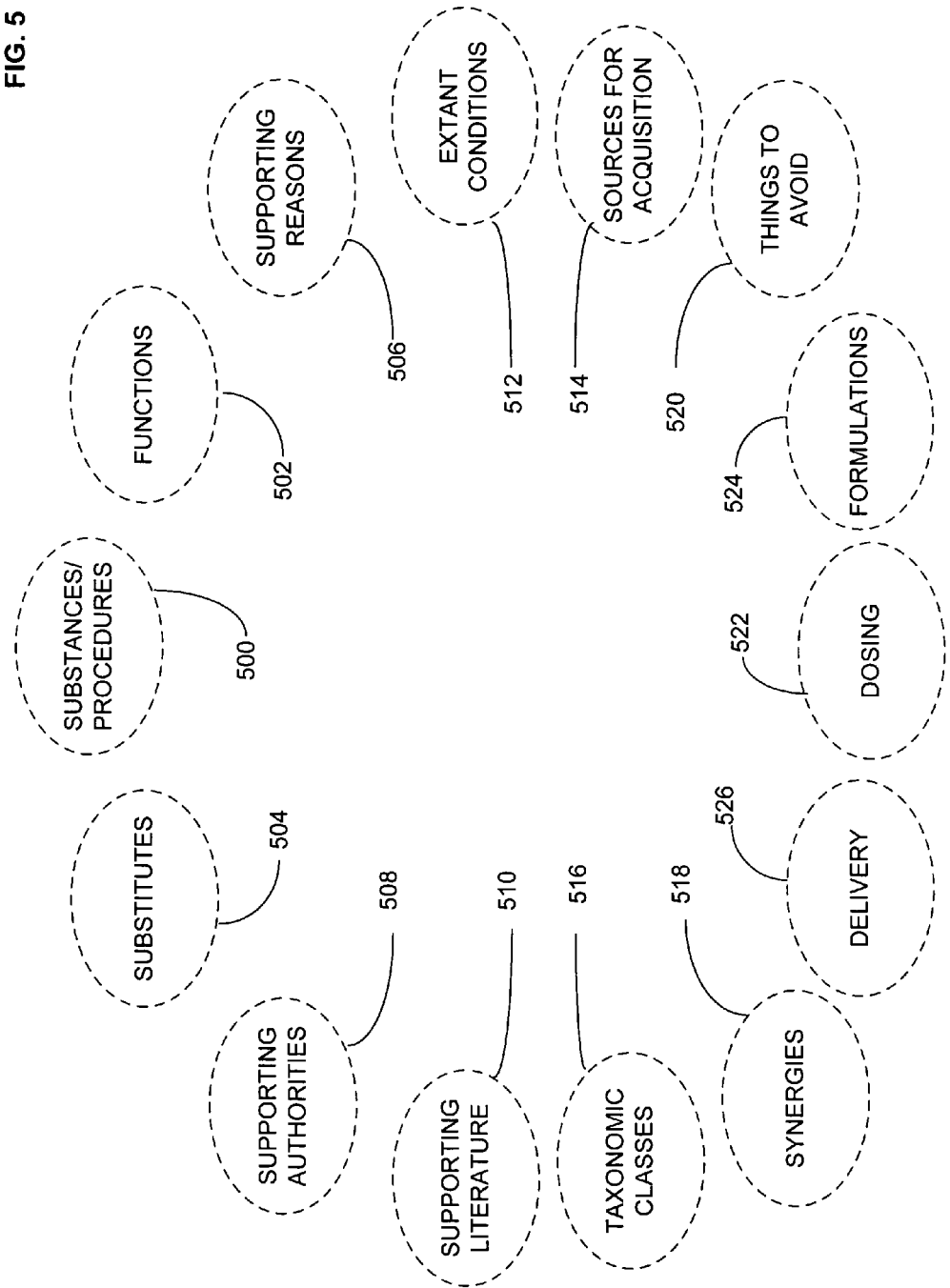
FIG. 5 depicts alternative exemplary aspects of embodiments.

FIG. 5 depicts a number of alternative exemplary topics which may be used in the data structure. The identity of a topic may be represented by a health regimen data entity, and association with a topic accomplished by use of an item of associative information. At least some health regimen data entities may be associated with topics of interest to the end-user 102 to provide a schema with which to begin use of the information in the data structure. Each of the topics is exemplary, but they serve to illustrate a particular application which is not limiting. An end-user 102 may start retrieving data from the data structure by starting with virtually any topic in the data structure. Each item of data stored in association with each topic may have been associated using an item of associative information with another item of data associated with the same topic or with another topic, such that an end-user 102 starting with an item of data in a particular topic, e.g., a name of Substance A under the topic Substances/Procedures 500, may choose to retrieve another item of data associated with Substance A via an item of associative information to a health regimen data entity associated with another topic, e.g., a function of Substance A, relief of joint pain, associated with the topic Functions 502. The end-user 102 may continue by selecting an item of data associated with a third topic, e.g., a Substitute B for Substance A for the relief of joint pain, associated with the topic Substitutes 504. The end-user 102 may continue in this fashion through all of the data items in the topics in the data structure associated via items of associative information to the selections of the end-user 102.

Although shown for clarity in FIG. 5 as discrete topics, generally, topics may be associated with or even be composed of other topics, and a given topic or reference to that topic may be associated with another discrete topic.

The topic 500, "Substances/Procedures," may include common, generic, commercial, and/or trade names and/or descriptions for pharmaceutical, nutraceutical, veterinary, dietary, and/or nutritional substances, procedures, processes, and/or practices of interest for use in a health regimen or regimens to an end-user 102.

The topic 502, "Functions," may include one or more descriptions of functions for which the substances of the topic 500, "Substances/Procedures" may be used by humans in connection with human physical and/or mental conditions, and/or veterinary purposes.

The topic 504, "Substitutes," may include common, generic, commercial, and/or trade names and/or descriptions for pharmaceutical, nutraceutical, veterinary, dietary, and/or nutritional substances, procedures, processes, and/or practices of interest for use in a health regimen or regimens to an end-user 102, which may be substituted to perform functions associated with the topic 502, "Functions."

The topic 506 "Supporting Reasons," may include explanations for the functionality of the substances/procedures and substitutes included in the topics 500, "Substances/Procedures" and 504, "Substitutes."

The topic 508, "Supporting Authorities," may include the identities and credentials of people and/or entities which endorse the use of substances/procedures and substitutes for various functions. The supporting authorities may include medical and/or veterinary professionals and/or experts of various kinds ("gurus"), and/or manufacturers and/or distributors of substances/procedures and substitutes. The topic 508, "Supporting Authorities," may also include testimonials and/or reports and/or anecdotal evidence from other end-users 102, and may include descriptors of factors associated with those end-users 102 to permit manual or automatic correlation of their experience with the potential experience of the end-user 102 consulting the data structure.

The topic 510, "Supporting Literature," may include references to published articles and/or other publicly available information, by citation and/or hyperlink and/or other reference means, e.g., referred journal articles and/or magazine articles and/or website articles, pertaining to the functionality of substances/procedures and substitutes.

The topic 512, "Extant Conditions," may include one or more selections of descriptors that describe internal physical and/or mental and/or environmental and/or spiritual and/or metaphysical factors of interest to the end-user 102 and of possible relevance to the functionality of substances/procedures and substitutes. Internal physical factors may include body temperature, medical condition, genetic information, and/or substances/procedures or substitutes ingested or to be ingested. Mental factors may include a diagnosed mental condition, a subjective mental state, genetic information, and/or substances/procedures or substitutes ingested or to be ingested. Environmental factors may include external temperature, humidity, barometric pressure, ambient light intensity, and, for some, the date, the positions of the planets, geographical factors such as those relevant to feng shui, and/or other factors relevant to disciplines, traditions, and arts considered relevant by the end-user 102 and/or by a contributor of information to the data structure and/or by a third-party authority such as an expert or a source for acquisition. Where feasible, values for external factors may be provided to the data structure in the form of health regimen data entities representing the output of instrumentation, e.g., weather instrumentation or medical instrumentation.

The topic 514, "Sources for Acquisition," may include identities of, contact information for, and/or channels of communication with persons and/or entities from which substances/procedures or substitutes may be purchased or otherwise acquired by the end-user 102. Such sources may pay to be included in the data structure in association with this topic.

The topic 516, "Taxonomic Classes," may include various categories with which substances/procedures and/or substitutes may be associated, e.g. acids, derivatives from X, etc.

The topic 518, "Synergies," may include substances/procedures, substitutes, activities, and/or extant conditions that, acting together with a substance or substitute, enhance the functionality of the substance or substitute; favorably change the amount or timing of the substance or substitute needed for the desired functionality; and/or provide one or more additional desirable functionalities beyond those associated with the substance or substitute taken by itself.

The topic 520, "Things to Avoid," may include substances/procedures, substitutes, activities, and/or extant conditions that, acting together with a substance or substitute, detracts from the functionality of the substance or substitute; unfavorably changes the amount or timing of the substance or substitute needed for the desired functionality; and/or provides one or more additional undesirable functionalities beyond those associated with the substance or substitute taken by itself.

The topic 522, "Dosing," may include information pertaining to the mode, amount, conditions, and/or timing of the delivery of a substance or substitute to achieve the desired functionality, along with synergies and things to avoid, e.g., 200 mg capsules of Substance A, taken twice daily when sunny and thrice daily when cloudy or raining; or once daily under any conditions no matter the weather, and never to be taken when Substance B has been taken within 24 hours. Beyond that simple example, the topic 522, "Dosing," may include a procedure for determining an amount and/or timing for the substance to be taken, rather than a simple fixed value, along with factors that give the end-user 102 options based on probabilities and other factors such as extant conditions, e.g., when the weather is hot and the end-user 102 is feeling irritable, an option to reduce a lithium dose by one pill per day, and if that does not work, by two pills per day, but never by more than two pills per day. These options and alternatives to them may also be accessed by associations with other health regimen data entities, including, e.g., hot days, lithium, and/or irritability.

The topic 524, "Formulations," may include information pertaining to the constituents of a substance, including but not limited to the identities of the constituents, the amounts of the constituents present per unit of the substance, and/or the method(s) for combining the constituents to form the substance. In particular, the amounts of the constituents may be represented by listing the amounts numerically, and/or by a formula or formulas from which each constituent amount may be derived either by the end-user 102 or by computational resources associated with the data structure. In an embodiment, the end-user 102 may follow items of associative information to health regimen data entities and/or additional information that provide information on the sources of formulary information, e.g., an article on an experiment, or on the instruments that provided the formulary information, e.g., an indication of what the underlying methodology of selection is at least partially based upon studies (e.g., animal studies, human studies, in silico studies), speculation, anecdotal information, historical accounts, traditions, cultural practices, native practices, etc.

The topic 526, "Delivery," may include information on methods of delivery, e.g., orally by capsule, orally by liquid dose, epidermally by patch, injection by syringe, and/or internally by timed release from an implanted reservoir, and on formulations, dose sizes, and dose timings associated with various delivery methods. Those skilled in the art will appreciate that substantially any of the delivery methods described herein may entail various release techniques, such as delayed, sustained, or pulsed release techniques.

Figure 6:
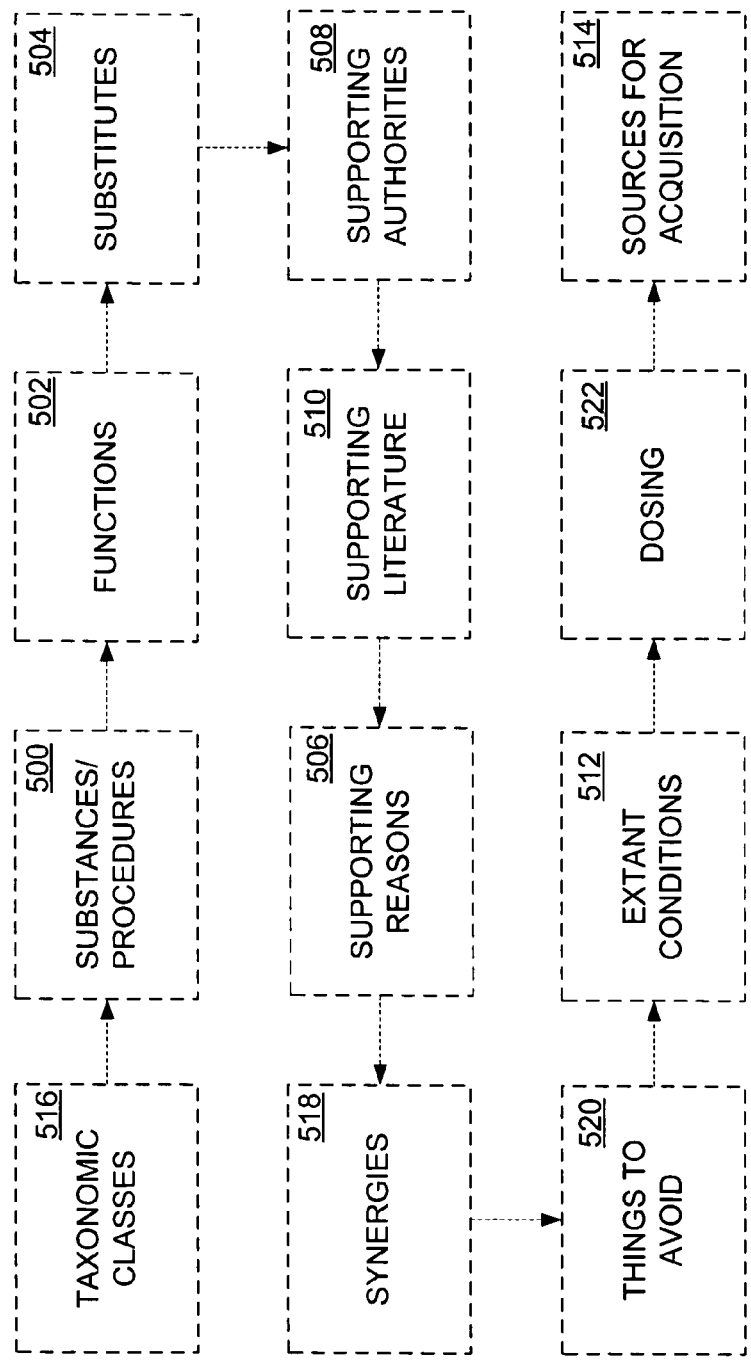
FIG. 6 depicts an exemplary view of aspects of an embodiment.

FIG. 6 depicts an exemplary way to view a pathway of an end-user 102 through data in the data structure. The end-user 102 in this exemplary view starts with taxonomic classes, e.g. vitamins, selects a vitamin, e.g., Vitamin X, and selects an associated function, e.g., increased energy. The end-user 102 finds a substitute for Vitamin X for increasing energy, e.g., Substance Y, refers to supporting authorities, e.g., a particular columnist for a magazine, supporting literature, e.g., an article in JAMA, and supporting reasons, e.g., a web-based explanation for the effects of Substance Y on energy. From there, the end-user 102 calls up information on synergies, e.g., Substance Z as being synergistic with Substance Y, providing increased memory when they are used together, along with things to avoid, e.g., not using Substance W in conjunction with Substance X because such conjunctive use causes impotence. The end-user 102 may consult "Extant Conditions" to learn that Substance X has an increased effect at lower altitudes and/or when certain planets are in a particular astrological configuration. The end-user 102 may consult the "Dosing" topic for information on dosing under various conditions, and she may peruse sources for acquisition to select a mode of purchase, to conclude the purchase, and to arrange for delivery.

Figure 7:
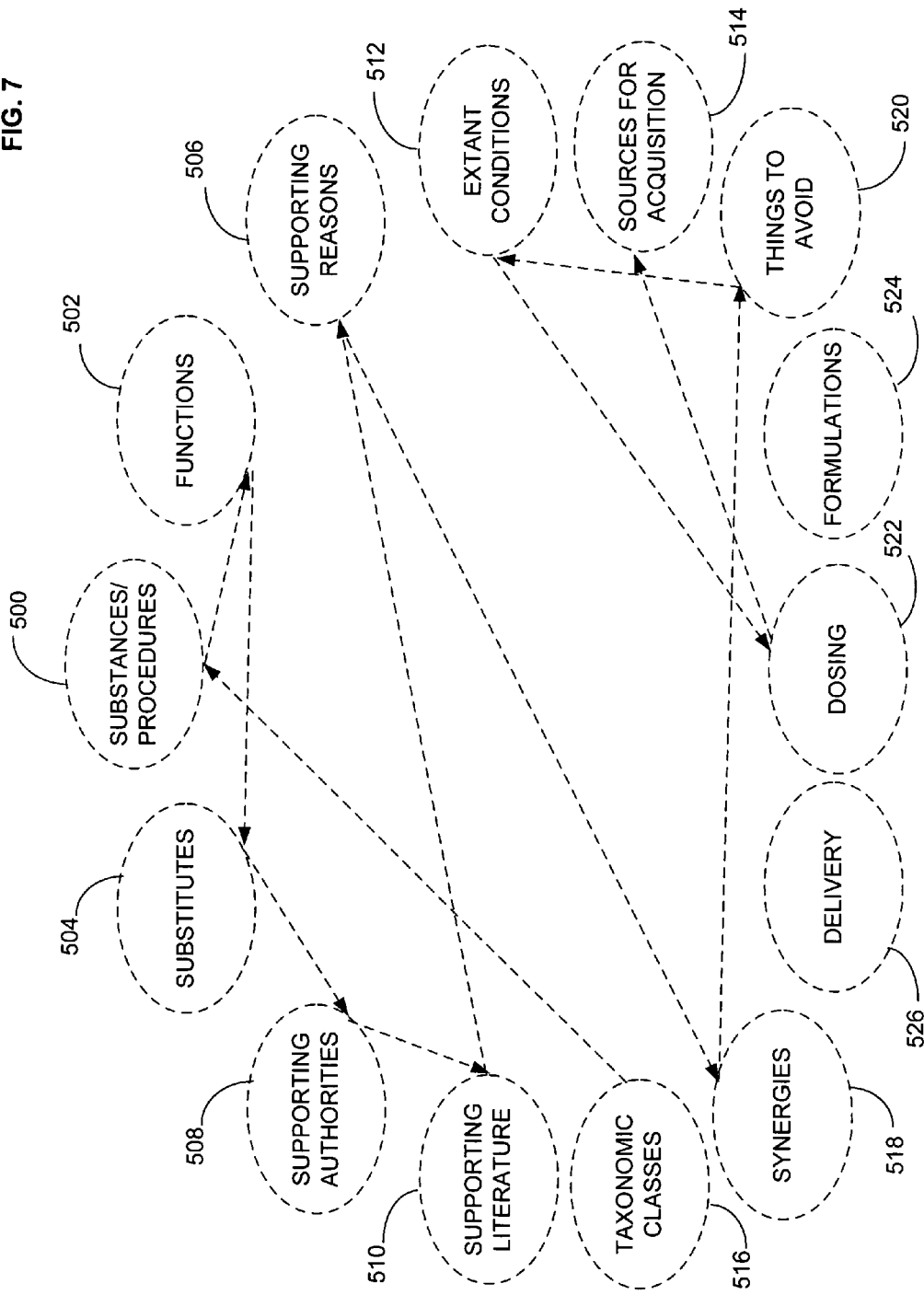
FIG. 7 depicts an alternative exemplary view of the aspects of the embodiment depicted in FIG. 6.

FIG. 7 depicts an alternative exemplary way to view the pathway of an end-user 102 through data in the data structure depicted in FIG. 6, using as a template the depiction of FIG. 5.

Figure 8:
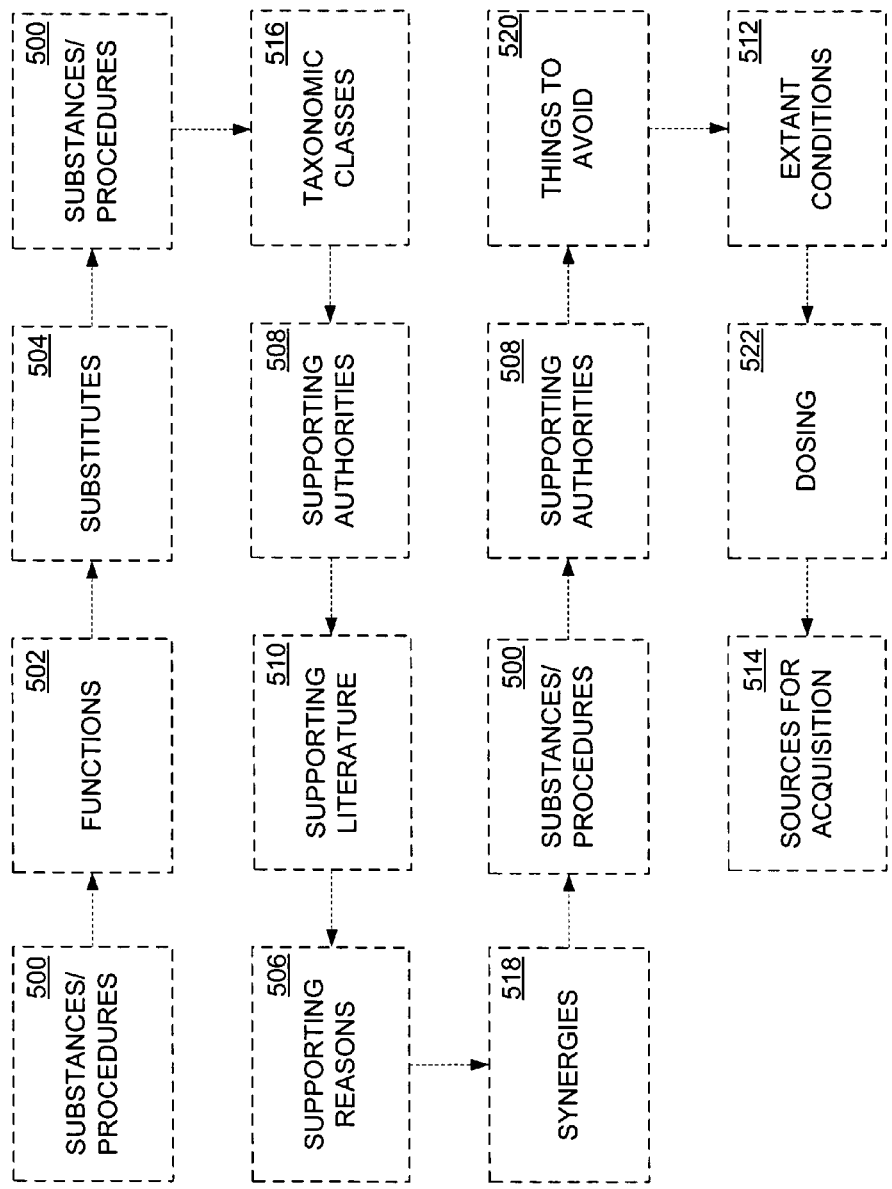
FIG. 8 depicts an exemplary view of aspects of an embodiment.

FIG. 8 depicts an exemplary view of the pathway of an end-user 102 through data in the data structure. The end-user 102 starts with a substance, e.g., Substance M, and looks up functions for Substance M, e.g., protection against cancer. The end-user 102 then looks up substitutes for Substance M for protection against cancer, e.g., Substance N. The end-user 102 then becomes interested in Substance N for other purposes. Going back to the topic "Substances/Procedures" to learn about Substance N, the end-user 102 learns that Substance N is a member of a particular taxonomic class, e.g. acids. The end-user 102 reassures himself of the efficacy of Substance N for some other purpose, e.g., prevention of hair loss, by consulting a supporting authority, e.g., a famous cancer researcher, supporting literature, e.g., a *Scientific American* article, and supporting reasons, e.g., a published explanation of why Substance N prevents hair loss. The end-user 102 retrieves information on synergies from the use of Substance N and Substance O, e.g., enhanced prevention of hair loss and fresher breath, and on things to avoid, e.g., the use of Substance N with, e.g., Substance P, which would lead to decreased efficacy for hair loss and extensive skin rashes. The end-user 102 calls up the effects of extant conditions on the use of Substance N, e.g., amplification of any already-present schizophrenia when certain planets are in a particular astrological configuration. The end-user 102 finishes by retrieving dosing information and proceeding to purchase through a source for acquisition.

Figure 9:
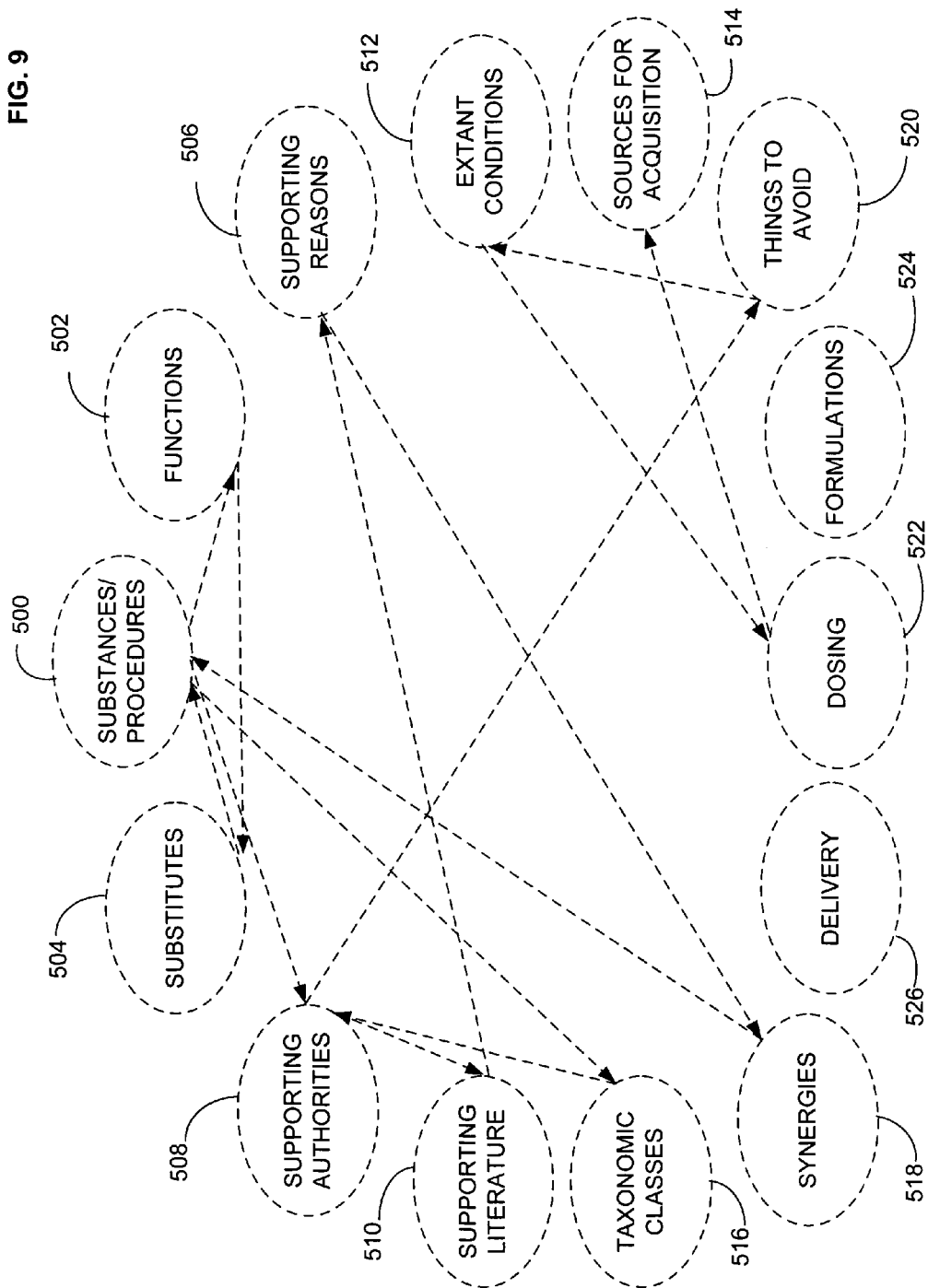
FIG. 9 depicts an alternative exemplary view of the aspects of the embodiment depicted in FIG. 8.

FIG. 9 depicts an alternative exemplary way to view the pathway of an end-user 102 through data in the data structure depicted in FIG. 8, using as a template the depiction of FIG. 5.

Figure 10:
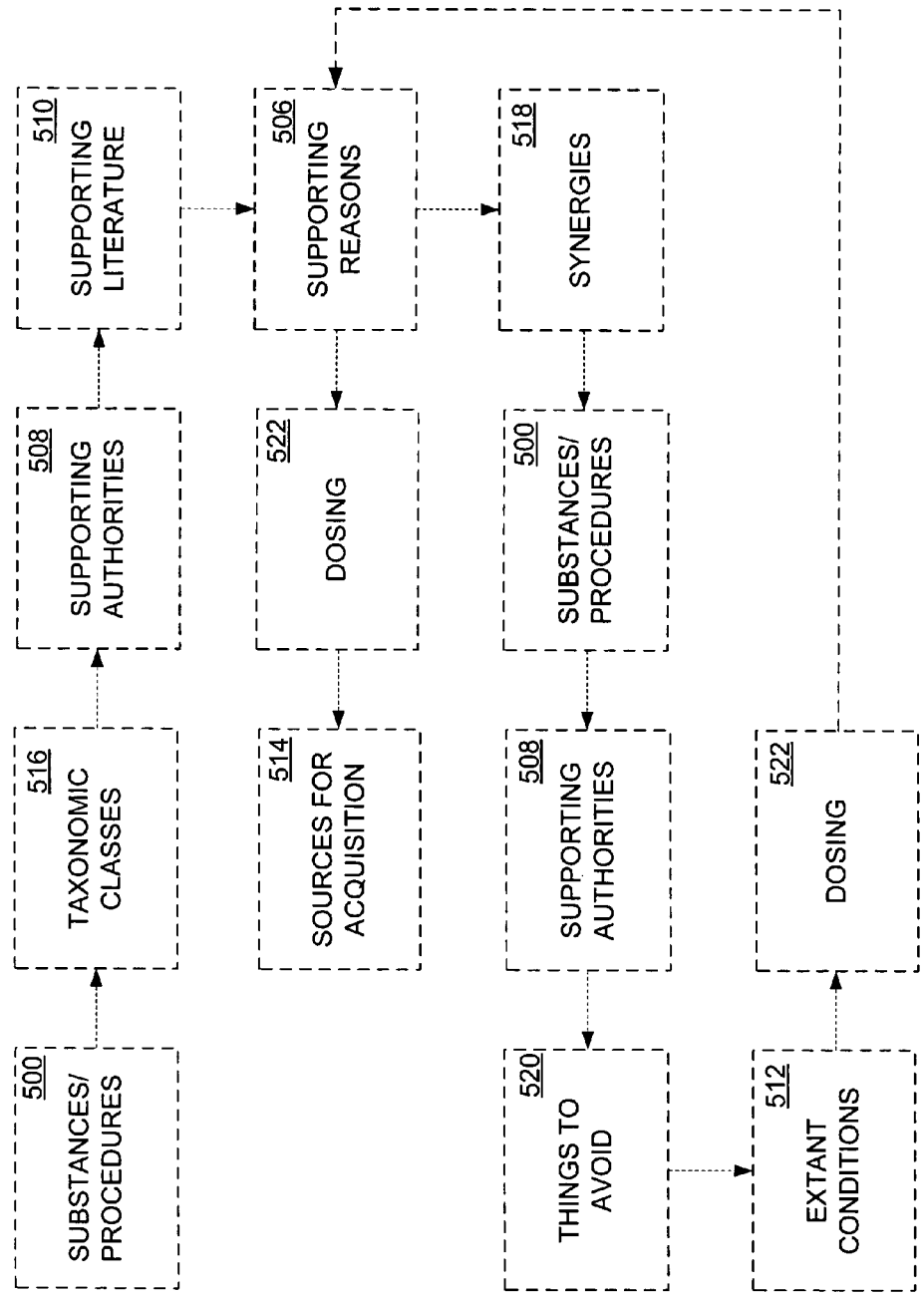
FIG. 10 depicts an exemplary view of aspects of an embodiment.

FIG. 10 depicts an exemplary way to view a branched pathway of an end-user 102 through data in the data structure. The end-user starts with a substance, e.g., Substance P, and looks up taxonomic classes associated with Substance P, e.g., water soluble vitamins. The end-user 102 then looks up supporting authorities for the use of water soluble vitamins for protection against cancer, such as a columnist in a well-known health magazine, and moves on to supporting literature, e.g., articles in reference journals, and supporting reasons, e.g., explanations of the functionality of water soluble vitamins for prevention of cancer. At this point, the end-user 102 remembers that a friend had been asking about the use of water soluble vitamins for other purposes, such as prevention of hair loss, especially in combination with certain procedures for their use. Leaving aside his original search, the end-user 102 takes up his friend's question and looks up synergies with regard to water soluble vitamins. After perusing synergies, he selects a procedure, e.g., taking a particular water soluble vitamin in conjunction with a food such as a particular fruit. He looks up supporting authorities for the efficacy of the water soluble vitamin in conjunction with the fruit for preventing hair loss, e.g., a medical society. He then checks for things to avoid, such as the use of a second vitamin that would reduce the effectiveness of the first vitamin and the fruit, and extant conditions, such as humidity, which might affect the usefulness of the water soluble vitamin. Finally, he looks at the appropriate dosing for the water soluble vitamin. Having investigated his friend's question, he returns to his original search. He had been looking up supporting reasons for the use of water soluble vitamins to prevent cancer. He resumes his research at that point and moves on to investigate appropriate dosing. Finally, he moves to sources for acquisition of the Substance P.

Figure 11:
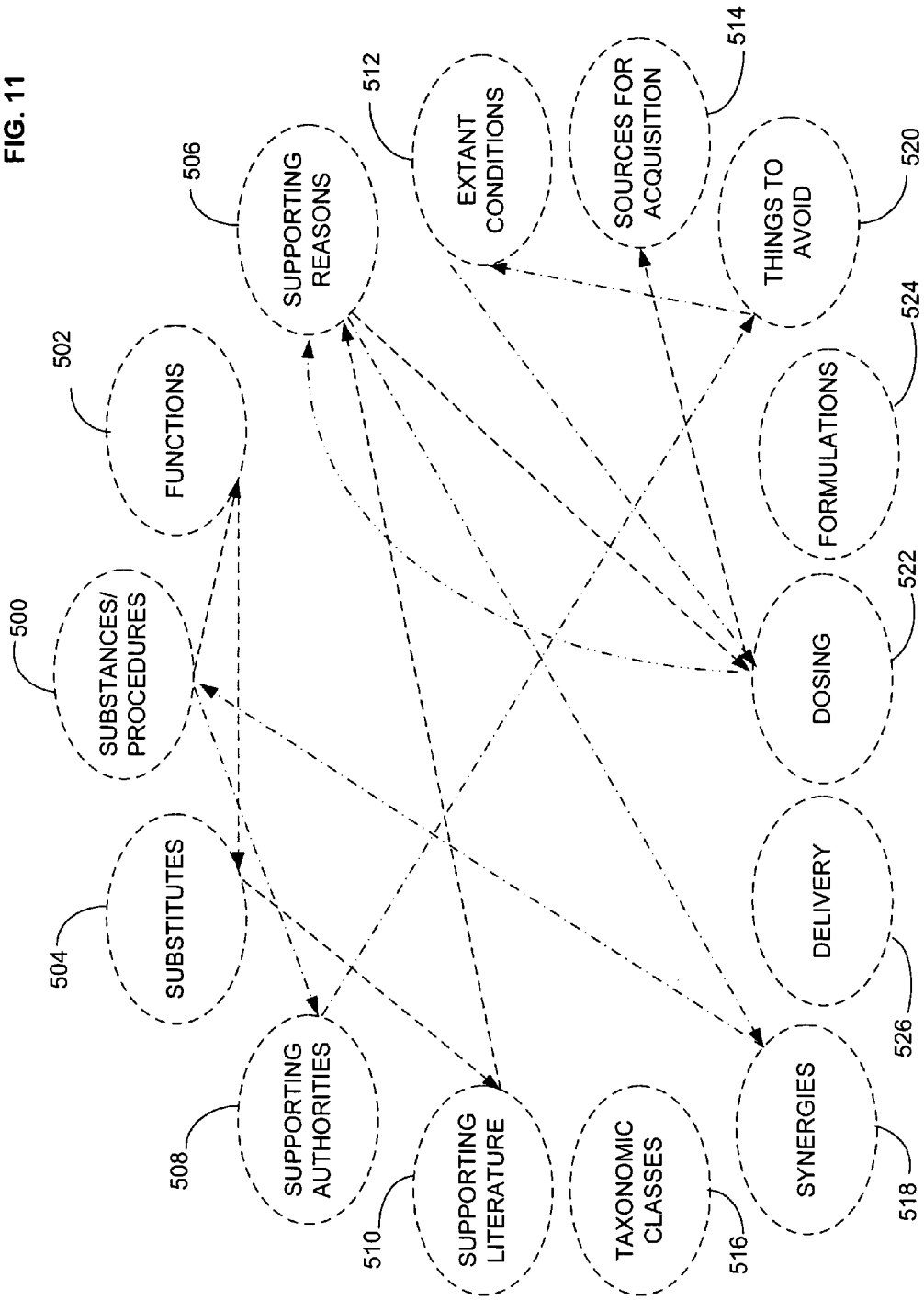
FIG. 11 depicts an alternative exemplary view of aspects of the embodiment depicted in FIG. 10.

FIG. 11 depicts an alternative exemplary way to view the pathway of an end-user 102 through data in the data structure depicted in FIG. 10, using as a template the depiction of FIG. 5.

Regarding FIGS. 1 through 11, the end-user 102 may search the data structure for patterns, finding correlations between health regimen data entities that would otherwise not be discoverable or that would be very difficult to discover. For example, the end-user 102 may search for effects of Substance A on skin rashes in conditions of high humidity, searching, among other health regimen data entities, those including anecdotal evidence from users of Substance A in high humidity, where the users of Substance A also had skin rashes and reported apparent effects of Substance A on those rashes. Such searches for correlations may include information and observations added to the data structure by all or any of the end-users 102, vendors 112, and/or publishers 120 using the data structure. Such searches may be used to test hypotheses about the efficacy and safety of pharmaceutical, nutraceutical, veterinary, dietary, and/or nutritional substances, procedures, processes, and/or practices of interest for use in a health regimen or regimens.

As mentioned above, end-users 102 may add health regimen data entities to the data structure to report experiences with the use of substances/procedures. For example, an end-user 102 may integrate a report of an experience, e.g., partial success with the use of Substance B for reduction of hair loss in low-humidity conditions but little success in conditions of high-humidity, by selecting pre-existing health regimen data entities with which to associate new health regimen data entities that represent relevant elements of his report, and/or by associating new health regimen data entities that represent relevant elements of his report with pre-existing annotations to pre-existing health regimen data entities added by other end-users 102 with similar reports. An end-user 102 may also add health regimen data entities representing the results of correlative searches such as those described above, e.g., by adding health regimen data entities representing the results of such a search and associating them with pre-existing health regimen data entities associated with, e.g., a Substance C used to alleviate heartburn in connection with particular dietary conditions.

In using the data structure, the end-user 102 may impose his own schema on the information searched and on the output of the search. The end-user 102 may explicitly include or exclude for search purposes health regimen data entities representing factors such as weather information or astrological information. He may include or exclude for search results reporting purposes various complexities, e.g., including tables of correlations for further study, but excluding such information and including only lists of ingredients and instructions for purposes of making a particular substance for use or lists of dosages to serve as input into medical dispensing devices, either indirectly through human input to devices or automatically through direct input of dosage information to devices.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 12:
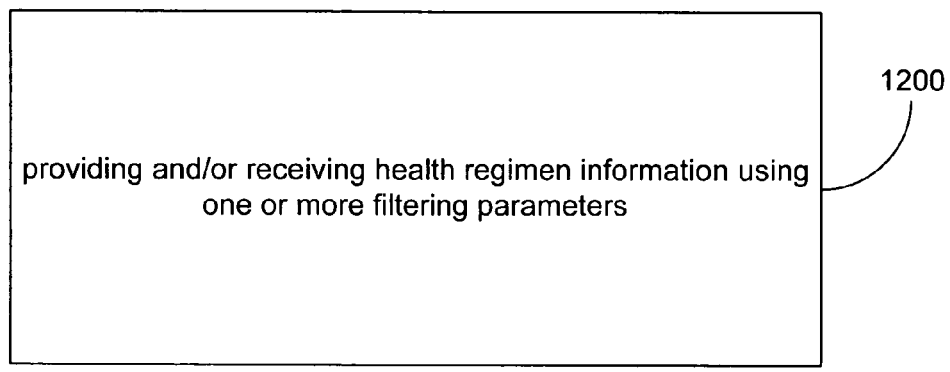
FIG. 12 depicts a high-level logic flowchart of an operational process.

FIG. 12 depicts a high-level logic flowchart of an operational process. Operation 1200 shows providing and/or receiving health regimen information using one or more filtering parameters (e.g., providing and/or receiving health regimen information using one or more filtering parameters, where an end-user interface device 104 and/or vendor interface device 114 and/or publisher interface device 122 and end-user logic 106 and/or vendor logic 116 and/or publisher logic 124 provide and/or receive for/from an end-user 102 and/or vendor 112 and/or publisher 120 a regimen for the use of dietary supplements for a physiological condition using one or more filtering parameters that select and/or exclude information on the basis of the medical condition of the end-user 102 and/or the availability of a particular brand of supplement from the vendor 112, where the health regimen information and/or the one or more filtering parameters are stored on computer 108 and/or computer 118 and/or computer 126). In some implementations, the one or more filtering parameters may result in something being added to and/or taken from and or changed within the health regimen information. However, in other implementations, it may be desired that the health regimen information be provided/recieved in more or less unfiltered form. Those skilled in the art will appreciate that such providing/receiving may be conceived of as the one or more filter parameters including one or more pass-through parameters.

In one general example of operation 1200, publisher interface device 122 and publisher logic 124 might provide the health regimen information using one or more filtering parameters by transmitting the health regimen information and filtering parameters to one or more other devices, such as end-user logic 106 of computer 108, where the transmitting might be through network 110. In one specific example of operation 1200, publisher interface device 122 and publisher logic 124 might provide the health regimen information using one or more filtering parameters by first filtering the health regimen information and thereafter transmitting the filtered health regimen information to one or more other devices, such as end-user logic 106 of computer 108. In another specific example of operation 1200, publisher interface device 122 and publisher logic 124 might provide the health regimen information using one or more filtering parameters by sequentially transmitting the health regimen information and the filtered health regimen information to one or more other devices, such as end-user logic 106 of computer 108.

In another general example of operation 1200, a device might receive health regimen information using one or more filtering parameters. In one specific example of operation 1200, end user logic 106 of computer 108 might receive health regimen information using one or more filtering parameters and thereafter filter the health regimen information. In another specific example of operation 1200, end user logic 106 of computer 108 might receive the health regimen information pre-filtered by the one or more filtering parameters.

In another general example of operation 1200, a device might provide the health regimen information using one or more filtering parameters through some type of interface. In one specific example of operation 1200, end user logic 106 may provide the health regimen information using one or more filter parameters to end user interface device 104.

In another general example of operation 1200, a device might receive the health regimen information using one or more filtering parameters through some type of interface. In one specific example of operation 1200, publisher logic 124 might accept the health regimen information using or the one or more filtering parameters through publisher interface device 122 (e.g., via accepting input from publisher 120).

Those skilled in the art will appreciate that the explicitly described examples involving the providing and/or receiving aspects of operation 1200 constitute only a few of the aspects illustrated by FIG. 12. Those skilled in the art also will appreciate that, as used herein, the phrase "provide and/or receive for/from" may typically be taken to be indicative of illustrated permutations/combinations of operations analogous to those described foregoing, unless context dictates otherwise.

Figure 13B:
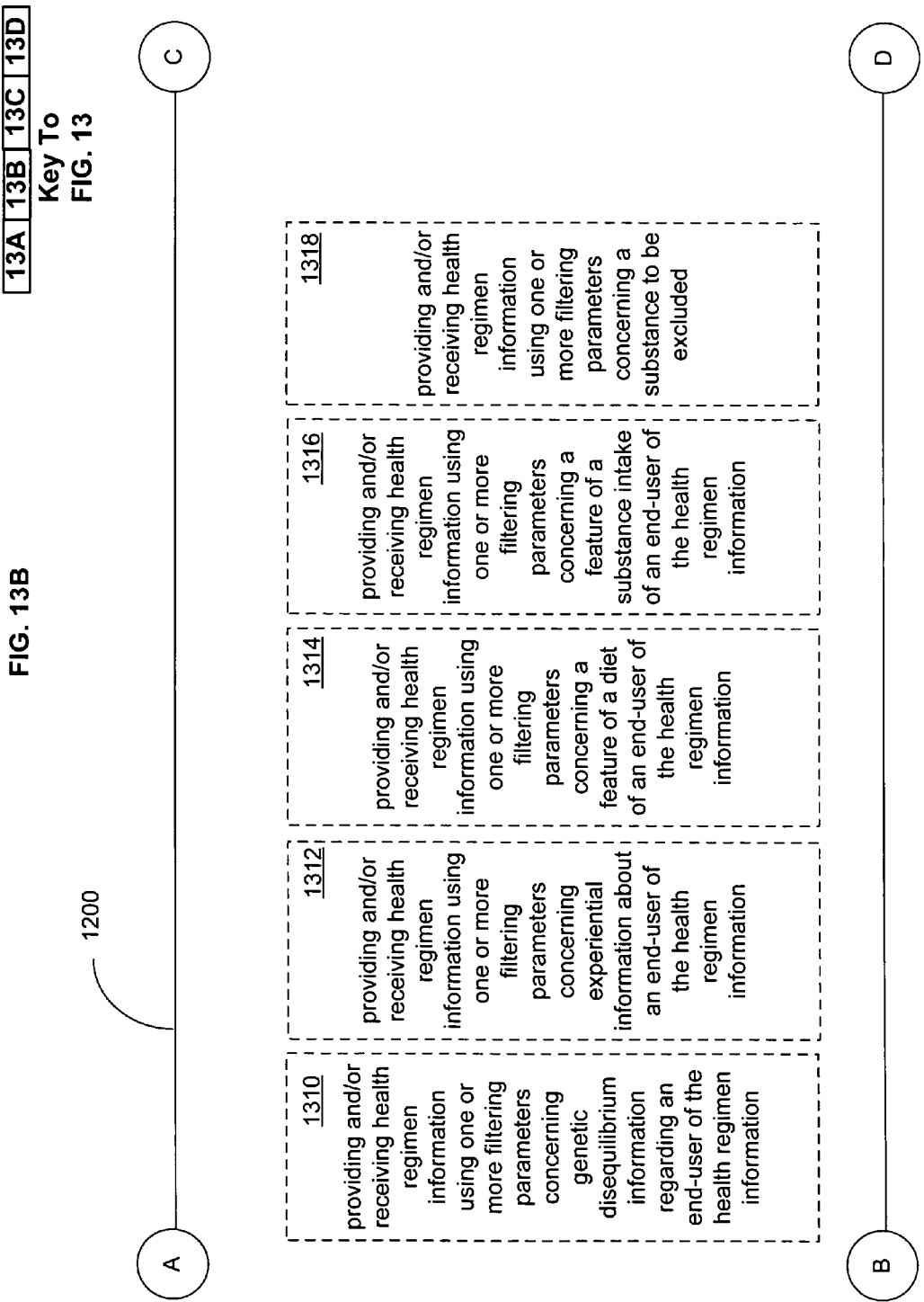
FIG. 13 shows several alternative implementations of the high-level logic flowchart of FIG. 12.

FIG. 13 shows several alternative implementations of the high-level logic flowchart of FIG. 12. Operation 1200—providing and/or receiving health regimen information using one or more filtering parameters—may include one or more of the following operations: 1300, 1302, 1304, 1306, 1308, 1310, 1312, 1314, 1316, 1318, 1320, 1322, 1324, 1326, 1328, 1330, 1332, 1334, 1336, 1338, and/or 1340.

Operation 1300 shows providing and/or receiving health regimen information using one or more filtering parameters concerning heredity information about an end-user of the health regimen information (e.g., providing and/or receiving health regimen information using one or more filtering parameters concerning heredity information about an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of substances for the amelioration of hair loss using one or more filtering parameters reflecting information about physiological characteristics of proximate blood relatives of the end-user 102, where the health regimen information and/or the one or more filtering parameters are stored on computer 108 and/or computer 118 and/or computer 126). For example, the heredity information need merely be an indicated item of heredity information, and could be, for example, associated with an objective item of heredity information (e.g., arising from scientific analysis), a proxied feature of an item of heredity information (e.g., designation of item of heredity information "X" in place of item of heredity information "Y"), a perceived/inferred item of heredity information (e.g., an item of heredity information chosen based on real and/or imagined criteria), an imagined item of heredity information (e.g., a hypothesized item of heredity information), and/or a suspected item of heredity information (e.g., based on certain traits, like inability to metabolize alcohol), etc.; the user might be an indicated user, and could be, for example, the user of a system or some hypothetical specified user having one or more defined traits.

Operation 1302 illustrates providing and/or receiving health regimen information using one or more filtering parameters concerning heredity information about one or more family members of an end-user of the health regimen information (e.g., providing and/or receiving health regimen information using one or more filtering parameters concerning heredity information about one or more family members of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of substances for a use of a process for weight loss using one or more filtering parameters reflecting information about physiological characteristics of proximate and distant blood relatives of the end-user 102, where the health regimen information and/or the one or more filtering parameters are stored on computer 108 and/or computer 118 and/or computer 126). For example, the heredity information need merely be an indicated item of heredity information, and could be, for example, associated with an objective item of heredity information (e.g., arising from scientific analysis), a proxied feature of an item of heredity information (e.g., designation of item of heredity information "X" in place of item of heredity information "Y"), a perceived/inferred item of heredity information (e.g., an item of heredity information chosen based on real and/or imagined criteria), an imagined item of heredity information (e.g., a hypothesized item of heredity information), and/or a suspected item of heredity information (e.g., based on certain traits, like inability to metabolize alcohol), etc.; the user might be an indicated user, and could be, for example, the user of a system or some hypothetical specified user having one or more defined traits.

Operation 1304 illustrates providing and/or receiving health regimen information using one or more filtering parameters concerning genetic profile information about an end-user of the health regimen information (e.g., providing and/or receiving health regimen information using one or more filtering parameters concerning genetic profile information about an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of dietary supplements for weight loss using one or more filtering parameters reflecting information about specific genetic profile characteristics of the end-user 102, where the health regimen information and/or the one or more filtering parameters are stored on computer 108 and/or computer 118 and/or computer 126). For example, the genetic profile need merely be an indicated genetic profile, and could be, for example, associated with an objective genetic profile (e.g., arising from scientific analysis), a proxied feature of a genetic profile (e.g., designation of gene "X" in place of gene "Y"), a perceived/inferred genetic profile (e.g., a profile chosen based on real and/or imagined criteria), an imagined genetic profile (e.g., a hypothesized genetic profile), and/or a suspected genetic profile (e.g., based on certain traits, like inability to metabolize alcohol), etc.; the user might be an indicated user, and could be, for example, the user of a system or some hypothetical specified user having one or more defined traits.

Operation 1306 shows providing and/or receiving health regimen information using one or more filtering parameters concerning genetic profile information about one or more family members of an end-user of the health regimen information (e.g., providing and/or receiving health regimen information using one or more filtering parameters concerning genetic profile information about one or more family members of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of lithium for a psychological condition using filtering parameters reflecting information about specific psychologically-relevant genetic profile characteristics of selected genetically-related relatives of the end-user 102, where the health regimen information and/or the one or more filtering parameters are stored on computer 108 and/or computer 118 and/or computer 126). For example, the genetic profile need merely be an indicated genetic profile, and could be, for example, associated with an objective genetic profile (e.g., arising from scientific analysis), a proxied feature of a genetic profile (e.g., designation of gene "X" in place of gene "Y"), a perceived/inferred genetic profile (e.g., a profile chosen based on real and/or imagined criteria), an imagined genetic profile (e.g., a hypothesized genetic profile), and/or a suspected genetic profile (e.g., based on certain traits, like inability to metabolize alcohol), etc.; the user might be an indicated user, and could be, for example, the user of a system or some hypothetical specified user having one or more defined traits.

Operation 1308 depicts providing and/or receiving health regimen information using one or more filtering parameters concerning inferred genetic signature information derived from genetic signature information about one or more family members of an end-user of the health regimen information (e.g., providing and/or receiving health regimen information using one or more filtering parameters concerning inferred genetic signature information derived from genetic signature information about one or more family members of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of lithium for a use of dietary supplements for weight loss using filtering parameters reflecting genetic characteristics of the end-user 102 that are inferred from specific weight-loss-relevant genetic characteristics of selected genetically-related relatives of the end-user 102, where the health regimen information and/or the one or more filtering parameters are stored on computer 108 and/or computer 118 and/or computer 126). For example, the inferred genetic signature need merely be an indicated inferred genetic signature, and could be, for example, associated with an objective inferred genetic signature (e.g., arising from scientific analysis), a proxied feature of an inferred genetic signature (e.g., designation of signature "X" in place of signature "Y"), a perceived inferred genetic signature (e.g., a profile chosen based on real and/or imagined criteria), an imagined inferred genetic signature (e.g., a hypothesized genetic profile), and/or a suspected inferred genetic signature (e.g., based on certain traits, like inability to metabolize alcohol), etc.; the user might be an indicated user, and could be, for example, the user of a system or some hypothetical specified user having one or more defined traits.

Operation 1310 shows providing and/or receiving health regimen information using one or more filtering parameters concerning genetic disequilibrium information regarding an end-user of the health regimen information (e.g., providing and/or receiving health regimen information using one or more filtering parameters concerning genetic disequilibrium information regarding an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of a process for amelioration of a blood disease of the end-user 102 using filtering parameters reflecting information about a physiological condition, the presence of which correlates significantly with an ethnicity of the end-user 102, where the health regimen information and/or the one or more filtering parameters are stored on computer 108 and/or computer 118 and/or computer 126). For example, the genetic disequilibrium information need merely be an indicated item of genetic disequilibrium information, and could be, for example, associated with an objective item of genetic disequilibrium information (e.g., arising from scientific analysis), a proxied feature of an item of genetic disequilibrium information (e.g., designation of item of genetic disequilibrium information "X" in place of item of genetic disequilibrium information "Y"), a perceived/inferred item of genetic disequilibrium information (e.g., a profile chosen based on real and/or imagined criteria), an imagined item of genetic disequilibrium information (e.g., a hypothesized genetic profile), and/or a suspected item of genetic disequilibrium information (e.g., based on certain traits, like inability to metabolize alcohol), etc.; the user might be an indicated user, and could be, for example, the user of a system or some hypothetical specified user having one or more defined traits.

Operation 1312 illustrates providing and/or receiving health regimen information using one or more filtering parameters concerning experiential information about an end-user of the health regimen information (e.g., providing and/or receiving health regimen information using one or more filtering parameters concerning experiential information about an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of a substance and a procedure for the reduction of hair-loss using filtering parameters reflecting information about an experience of the substance and a procedure for the reduction of hair-loss by a user, where the health regimen information and/or the one or more filtering parameters are stored on computer 108 and/or computer 118 and/or computer 126). For example, the experiential information need merely be an indicated item of experiential information, and could be, for example, associated with an objective item of experiential information, a proxied item of experiential information, a perceived/imagined item of experiential information (e.g., a feeling of anxiety after taking a substance), and/or a suspected item of experiential information, etc.; the user might be an indicated user, and could be, for example, the user of a system or some hypothetical specified user having one or more defined traits.

Operation 1314 depicts providing and/or receiving health regimen information using one or more filtering parameters concerning a feature of a diet of an end-user of the health regimen information (e.g., providing and/or receiving health regimen information using one or more filtering parameters concerning a feature of a diet of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of dietary supplements for weight loss using filtering parameters reflecting information about recent and/or prospective food intake by the end-user 102, where the health regimen information and/or the one or more filtering parameters are stored on computer 108 and/or computer 118 and/or computer 126). For example, the feature of a diet need merely be an indicated feature of a diet, and could be, for example, associated with an objective feature of a diet, a proxied feature of a diet, a perceived/imagined feature of a diet (e.g., indication of a "low fat" diet), and/or a suspected feature of a diet, etc.; the user might be an indicated user, and could be, for example, the user of a system or some hypothetical specified user having one or more defined traits.

Operation 1316 shows providing and/or receiving health regimen information using one or more filtering parameters concerning a feature of a substance intake of an end-user of the health regimen information (e.g., providing and/or receiving health regimen information using one or more filtering parameters concerning a feature of a substance intake of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of lithium for a psychological condition using filtering parameters reflecting information about recent drug use by the end-user 102, where the health regimen information and/or the one or more filtering parameters are stored on computer 108 and/or computer 118 and/or computer 126). For example, the feature of a substance intake need merely be an indicated feature of a substance intake, and could be, for example, associated with an objective feature of a substance intake, a proxied feature of a substance intake (e.g., poppy seeds instead of an opiate), a perceived feature of a substance intake, an imagined feature of a substance intake, and/or a suspected feature of a substance intake, etc.; the user might be an indicated user, and could be, for example, the user of a system or some hypothetical specified user having one or more defined traits.

Operation 1318 illustrates providing and/or receiving health regimen information using one or more filtering parameters concerning a substance to be excluded (e.g., providing and/or receiving health regimen information using one or more filtering parameters concerning a substance to be excluded, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of a substance to address an infection using filtering parameters reflecting one or more substances to which the end-user 102 is allergic, where the health regimen information and/or the one or more filtering parameters are stored on computer 108 and/or computer 118 and/or computer 126). For example, the substance to be excluded need merely be an indicated substance to be excluded, and could be, for example, associated with an objective substance to be excluded, a proxied substance to be excluded (e.g., peanut butter instead of peanuts), a perceived substance to be excluded, an imagined substance to be excluded, and/or a suspected substance to be excluded, etc.; the user might be an indicated user, and could be, for example, the user of a system or some hypothetical specified user having one or more defined traits.

Operation 1320 shows providing and/or receiving health regimen information using one or more filtering parameters concerning a current and/or anticipated activity of an end-user of the health regimen information (e.g., providing and/or receiving health regimen information using one or more filtering parameters concerning a current and/or anticipated activity of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of a substance to address an allergy using filtering parameters reflecting information about travel to an area with a high concentration of an allergen and/or where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen taking into account future plans, e.g., to run a marathon next week or, e.g., to engage in a bout of drinking alcohol at a future instance in time, where the health regimen information and/or the one or more filtering parameters are stored on computer 108 and/or computer 118 and/or computer 126). For example, the current and/or anticipated activity need merely be an indicated current and/or anticipated activity, and could be, for example, associated with an objective current and/or anticipated activity, a proxied current and/or anticipated activity (e.g., jogging instead of running), a perceived current and/or anticipated activity, an imagined current and/or anticipated activity, and/or a suspected current and/or anticipated activity, etc.; the user might be an indicated user, and could be, for example, the user of a system or some hypothetical specified user having one or more defined traits.

Operation 1322 depicts providing and/or receiving health regimen information using one or more filtering parameters concerning a comparison of alternative substances and/or procedures regarding an economic cost and/or a reduced effect and/or an enhanced effect (e.g., providing and/or receiving health regimen information using one or more filtering parameters concerning a comparison of alternative substances and/or procedures regarding an economic cost and/or a reduced effect and/or an enhanced effect, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of dietary supplements for weight loss by the end-user 102 using filtering parameters reflecting information about comparative monetary costs of alternative supplements and/or comparative reduction of efficacy with regard to weight loss and/or comparative enhancement of efficacy with regard to weight loss, and/or where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a reminder not to take and/or serve grapefruit juice responsive to a trigger independent of individual attributes of a health regimen component, where the trigger might be, for example, time of day or other interval, where the health regimen information and/or the one or more filtering parameters are stored on computer 108 and/or computer 118 and/or computer 126). For example, the economic cost and/or a reduced effect and/or an enhanced effect need merely be an indicated economic cost and/or a reduced effect and/or an enhanced effect, and could be, for example, associated with an objective economic cost and/or a reduced effect and/or an enhanced effect, a proxied economic cost and/or a reduced effect and/or an enhanced effect (e.g., an opportunity cost instead of a monetary cost; an effect limited in scope instead of an effect reduced overall, such as weight loss in the stomach area only instead of weight loss overall; and/or an effect enhanced in scope instead of an effect enhanced in magnitude, such as hair restoration all over the body instead of hair restoration on the head only), a perceived economic cost and/or a reduced effect and/or an enhanced effect, an imagined economic cost and/or a reduced effect and/or an enhanced effect, and/or a suspected economic cost and/or a reduced effect and/or an enhanced effect, etc.; the user might be an indicated user, and could be, for example, the user of a system or some hypothetical specified user having one or more defined traits.

Operation 1324 shows providing and/or receiving health regimen information using one or more filtering parameters concerning an update to the health regimen information (e.g., providing and/or receiving health regimen information using one or more filtering parameters concerning an update to the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of a substance for an amelioration of hair loss in the end-user 102 using filtering parameters reflecting information about the timing and/or content of desired updates to the regimen as improvements are discovered and/or detected, where the health regimen information and/or the one or more filtering parameters are stored on computer 108 and/or computer 118 and/or computer 126). For example, the update need merely be an indicated update, and could be, for example, associated with an objective update, a proxied update (e.g., an update concerning poppy seeds instead of an update concerning an opiate), a perceived update, an imagined update, and/or a suspected update, etc.; the user might be an indicated user, and could be, for example, the user of a system or some hypothetical specified user having one or more defined traits.

Operation 1326 illustrates providing and/or receiving health regimen information using one or more filtering parameters concerning an update to information that is relevant to a use of the health regimen information (e.g., providing and/or receiving health regimen information using one or more filtering parameters concerning an update to information that is relevant to a use of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of a dietary substance for weight loss by the end-user 102 using filtering parameters reflecting information about the timing and/or content of desired updates showing advantages and/or drawbacks to the use of the regimen, where the health regimen information and/or the one or more filtering parameters are stored on computer 108 and/or computer 118 and/or computer 126). For example, the update need merely be an indicated update, and could be, for example, associated with an objective update, a proxied update (e.g., an update concerning poppy seeds instead of an update concerning an opiate), a perceived update, an imagined update, and/or a suspected update, etc.; the user might be an indicated user, and could be, for example, the user of a system or some hypothetical specified user having one or more defined traits.

Operation 1328 shows providing and/or receiving health regimen information using one or more filtering parameters concerning an alert relevant to a use of the health regimen information (e.g., providing and/or receiving health regimen information using one or more filtering parameters concerning an alert relevant to a use of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of lithium for a psychological condition of the end-user 102 using filtering parameters reflecting information about the timing and/or content of desired information concerning dangers associated with the use of the regimen, where the health regimen information and/or the one or more filtering parameters are stored on computer 108 and/or computer 118 and/or computer 126). For example, the alert need merely be an indicated alert, and could be, for example, associated with an objective alert, a proxied alert (e.g., an alert concerning poppy seeds instead of an alert concerning an opiate), a perceived alert, an imagined alert, and/or a suspected alert, etc.; the user might be an indicated user, and could be, for example, the user of a system or some hypothetical specified user having one or more defined traits.

Operation 1330 depicts providing and/or receiving health regimen information using one or more filtering parameters concerning credibility information relevant to a use of the health regimen information (e.g., providing and/or receiving health regimen information using one or more filtering parameters concerning credibility information relevant to a use of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of lithium for a psychological condition of the end-user 102 using filtering parameters reflecting information about a credibility rating on a scale of 0 to 10, with 0 representing an absence of reasons to give weight to the health regimen information and 10 representing a predetermined number of endorsements from trusted authorities and/or reports of scientifically conducted studies confirming the health regimen information, where the health regimen information and/or the one or more filtering parameters are stored on computer 108 and/or computer 118 and/or computer 126). For example, the credibility information need merely be an indicated item of credibility information, and could be, for example, associated with an objective item of credibility information, a proxied item of credibility information (e.g., an item of credibility information concerning information on the use of poppy seeds instead of an item of credibility information concerning information on the use of an opiate), a perceived item of credibility information, an imagined item of credibility information, and/or a suspected item of credibility information, etc.; the user might be an indicated user, and could be, for example, the user of a system or some hypothetical specified user having one or more defined traits.

Operation 1332 shows providing and/or receiving health regimen information using one or more filtering parameters concerning a reference to information relevant to a use of the health regimen information (e.g., providing and/or receiving health regimen information using one or more filtering parameters concerning a reference to information relevant to a use of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of dietary supplements for weight loss by the end-user 102 using filtering parameters reflecting information about an endorsement of the regimen by a trusted authority, where the health regimen information and/or the one or more filtering parameters are stored on computer 108 and/or computer 118 and/or computer 126). For example, the reference need merely be an indicated reference, and could be, for example, associated with an objective reference, a proxied reference (e.g., a reference to information on the use of poppy seeds instead of a reference to information on the use of an opiate), a perceived reference, an imagined reference, and/or a suspected reference, etc.; the user might be an indicated user, and could be, for example, the user of a system or some hypothetical specified user having one or more defined traits.

Operation 1334 illustrates providing and/or receiving health regimen information using one or more filtering parameters concerning a variation of the health regimen information (e.g., providing and/or receiving health regimen information using one or more filtering parameters concerning a variation of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of a substance to ameliorate hair loss in end-user 102 using filtering parameters reflecting information about variations in, for example, dosage and/or timing and/or conditions in which the substance is to be applied based on environmental or dietary factors, where the health regimen information and/or the one or more filtering parameters are stored on computer 108 and/or computer 118 and/or computer 126). For example, the variation need merely be an indicated variation, and could be, for example, associated with an objective variation, a proxied variation (e.g., a variation of information on the use poppy seeds instead of variation of information on the use of an opiate), a perceived variation, an imagined variation, and/or a suspected variation, etc.; the user might be an indicated user, and could be, for example, the user of a system or some hypothetical specified user having one or more defined traits.

Operation 1336 depicts providing and/or receiving health regimen information using one or more filtering parameters concerning a medical condition of an end-user of the health regimen information (e.g., providing and/or receiving health regimen information using one or more filtering parameters concerning a medical condition of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of dietary supplements for weight loss in the end-user 102 using filtering parameters reflecting information about a heart condition in the end-user 102, where the health regimen information and/or the one or more filtering parameters are stored on computer 108 and/or computer 118 and/or computer 126). For example, the medical condition need merely be an indicated medical condition, and could be, for example, associated with an objective medical condition, a proxied medical condition (e.g., enthused instead of manic), a perceived medical condition, an imagined medical condition, and/or a suspected medical condition, etc.; the medical condition might include a physiological condition and/or a psychological condition; the user might be an indicated user, and could be, for example, the user of a system or some hypothetical specified user having one or more defined traits.

Operation 1338 shows providing and/or receiving health regimen information using one or more filtering parameters concerning a condition external to an end-user of the health regimen information (e.g., providing and/or receiving health regimen information using one or more filtering parameters concerning a condition external to an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of lithium for a psychological condition in the end-user 102 using filtering parameters reflecting information about temperature and humidity conditions at the location in which the lithium is expected to be used, and/or where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen including a procedure for using a medication reactive with acid aldehyde to alleviate the long-term effects of alcohol, or an optional procedure for restoration of a water soluble electrolyte, vitamin, etc., where the health regimen information and/or the one or more filtering parameters are stored on computer 108 and/or computer 118 and/or computer 126). For example, the condition external to a user might entail an indicated condition external to the user, and could be, for example, associated with an objective, perceived, and/or a suspected environmental condition and/or an objective, perceived, or suspected aspect external to the action and/or effect of health regimen information (e.g., a social perception that taking a particular type/brand of nutracuetical is "cool", etc.); the user might be an indicated user, and could be, for example, the user of a system or some hypothetical specified user having one or more defined traits.

Operation 1340 depicts providing and/or receiving health regimen information using one or more filtering parameters concerning information about a physiological process of an end-user of the health regimen information (e.g., providing and/or receiving health regimen information using one or more filtering parameters concerning information about a physiological process of an end-user of the health regimen information, where an end-user interface device 104 and/or vendor interface device 114 and/or publisher interface device 122 and end-user logic 106 and/or vendor logic 116 and/or publisher logic 124 provide and/or receive for/from end-user 102 and/or vendor 112 and/or publisher 120 a regimen for a use of lithium for a psychological condition using one or more filtering parameters that reflect how the end-user has been driving his or her homeostatic mechanisms within a relevant period of time, where the health regimen information and/or the one or more filtering parameters are stored on computer 108 and/or computer 118 and/or computer 126). For example, the physiological process need merely be an indicated physiological process, and could be, for example, associated with an objective physiological process, a proxied physiological process (e.g., enthused instead of manic), a perceived physiological process, an imagined physiological process, and/or a suspected physiological process, etc.; the user might be an indicated user, and could be, for example, the user of a system or some hypothetical specified user having one or more defined traits. Examples of homeostatic mechanisms include temperature regulation mechanisms, glucose blood level regulation mechanisms, insulin blood level regulation mechanisms, electrolyte level regulation mechanisms, and/or intestinal flora/fauna regulation mechanisms. Examples of driving homeostatic mechanisms might include historical data associated with dietary activities/environmental activities/physical activities known to have effects on such homeostatic mechanisms over a period of time.

Figure 14:
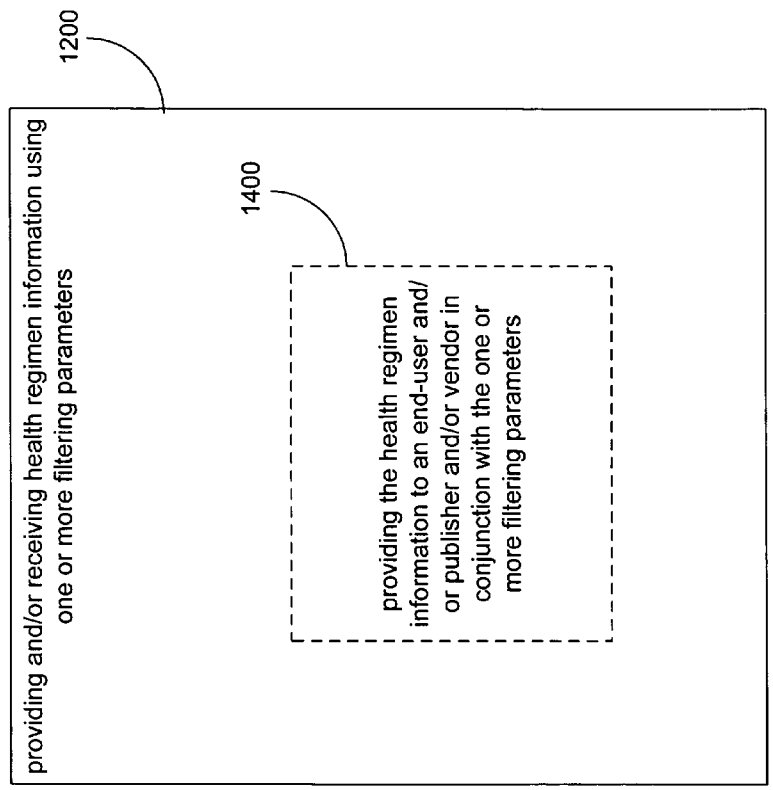
FIG. 14 shows an alternative implementation of the high-level logic flowchart of FIG. 12.

FIG. 14 shows an alternative implementation of the high-level logic flowchart of FIG. 12. The depicted operational process may include operation 1200 and/or operation 1400. Operation 1200 is described in conjunction with FIG. 12. Operation 1200 and operation 1400 may be performed in any order and/or at least in part in parallel. Operation 1400 shows providing the health regimen information to an end-user and/or publisher and/or vendor in conjunction with the one or more filtering parameters (e.g., providing the health regimen information to an end-user 102 and/or publisher 120 and/or vendor 112 in conjunction with the one or more filtering parameters, where an end-user interface device 104 and/or vendor interface device 114 and/or publisher interface device 122 and end-user logic 106 and/or vendor logic 116 and/or publisher logic 124 is provided in a regimen for the use of lithium for a psychological condition of the end-user 102 by a selection of the information to be provided according to a set of filtering parameters, where the health regimen information and/or the one or more filtering parameters are stored on computer 108 and/or computer 118 and/or computer 126). One aspect includes, e.g., a publisher interface device 122 and publisher logic 124 receiving health regimen information using one or more filtering parameters according to operation 1200 and then providing to an end-user interface device 104 and end-user logic 106 health regimen information in conjunction with the one or more filtering parameters, according to operation 1400 (e.g., in one implementation, the health regimen information may be presented through a graphical user interface (GUI) feature of end-user interface device 104 and end-user logic 106 with the one or more filtering parameters clearly and explicitly labeled, while in another implementation, the health regimen information, provided in conjunction with the one or more filtering parameters, may be presented through a GUI of end-user interface device 104 and end-user logic 106 without the filtering parameters being explicitly labeled). Another aspect includes, e.g., a publisher interface device 122 and publisher logic 124 providing health regimen information using one or more filtering parameters to the network 110 according to operation 1200 and then providing to a vendor interface device 114 and vendor logic 116 health regimen information in conjunction with the one or more filtering parameters according to operation 1400 (e.g., in one implementation, the network 110 provides the health regimen information through a GUI of vendor interface device 114 and vendor logic 116 with the one or more filtering parameters clearly and explicitly labeled, while in another implementation, the health regimen information, provided in conjunction with the one or more filtering parameters, may be presented through a GUI of vendor interface device 114 and vendor logic 116 without the filtering parameters being explicitly labeled). Those skilled in the art will appreciate that other combinations of providing and/or receiving health regimen information among various interface devices and logic are possible, but they are not described here for the sake of clarity. Those skilled in the art will appreciate that operations 1200 and 1400 as described herein, and as illustrated herein by the sequential examples and in other aspects for which examples are implicitly provided for the sake of clarity, may be performed at least in part in parallel.

Figure 15:
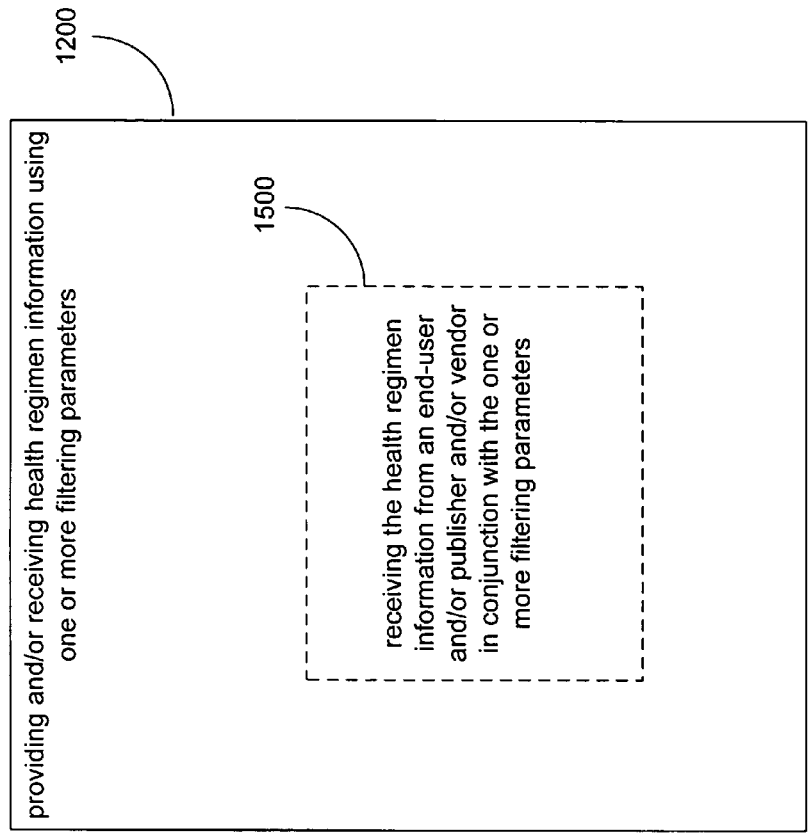
FIG. 15 depicts an alternative implementation of the high-level logic flowchart of FIG. 12

FIG. 15 depicts an alternative implementation of the high-level logic flowchart of FIG. 12. The depicted operational process may include operation 1200 and/or operation 1500. Operation 1200 is described in conjunction with FIG. 12. Operation 1200 and operation 1500 may be performed in any order and/or at least in part in parallel. Operation 1500 depicts receiving the health regimen information from an end-user and/or publisher and/or vendor in conjunction with the one or more filtering parameters (e.g., receiving the health regimen information from an end-user 102 and/or publisher 120 and/or vendor 112 in conjunction with the one or more filtering parameters, where an end-user interface device 104 and/or vendor interface device 114 and/or publisher interface device 122 and end-user logic 106 and/or vendor logic 116 and/or publisher logic 124 receives a regimen for the use of lithium for a psychological condition of the end-user 102 by a selection of the information to be received according to a set of filtering parameters, where the health regimen information and/or the one or more filtering parameters are stored on computer 108 and/or computer 118 and/or computer 126). One aspect includes, e.g., a publisher interface device 122 and publisher logic 124 receiving from a vendor interface device 114 and vendor logic 116 health regimen information using one or more filtering parameters according to operation 1200 and then an end-user interface device 104 and end-user logic 106 receiving health regimen information in conjunction with the one or more filtering parameters according to operation 1500 (e.g., in one implementation, an end-user interface device 104 and end-user logic 106 may receive health regimen information via the network 110, with the health regimen information being received through a GUI of end-user interface device 104 with the filtering parameters clearly and explicitly labeled, while in another implementation, the health regimen information, received in conjunction with the one or more filtering parameters, may be presented through a GUI of end-user interface device 104 and end-user logic 116 without the filtering parameters being explicitly labeled). Another aspect includes, e.g., a vendor interface device 114 and vendor logic 116 providing health regimen information using one or more filtering parameters via the network 110 according to operation 1200 and then an end-user interface device 104 and end-user logic 106 receiving health regimen information in conjunction with the one or more filtering parameters according to operation 1500 (e.g., in one implementation, an end-user interface device 104 and end-user logic 106 may receive health regimen information in conjunction with the one or more filtering parameters via the network 110, with the health regimen information received through a GUI of end-user interface device 104 with the filtering parameters clearly and explicitly labeled, while in another implementation, the health regimen information, received in conjunction with the one or more filtering parameters, may be received through a GUI of end-user interface device 104 and end-user logic 116 without the filtering parameters being explicitly labeled). Those skilled in the art will appreciate that other combinations of providing and/or receiving health regimen information among various interface devices and logic are possible, but they are not described here for the sake of clarity. Those skilled in the art will appreciate that operations 1200 and 1500 as described herein, and as illustrated herein by the sequential examples and in other aspects for which examples are implicitly provided for the sake of clarity, may be performed at least in part in parallel.

Figure 16:
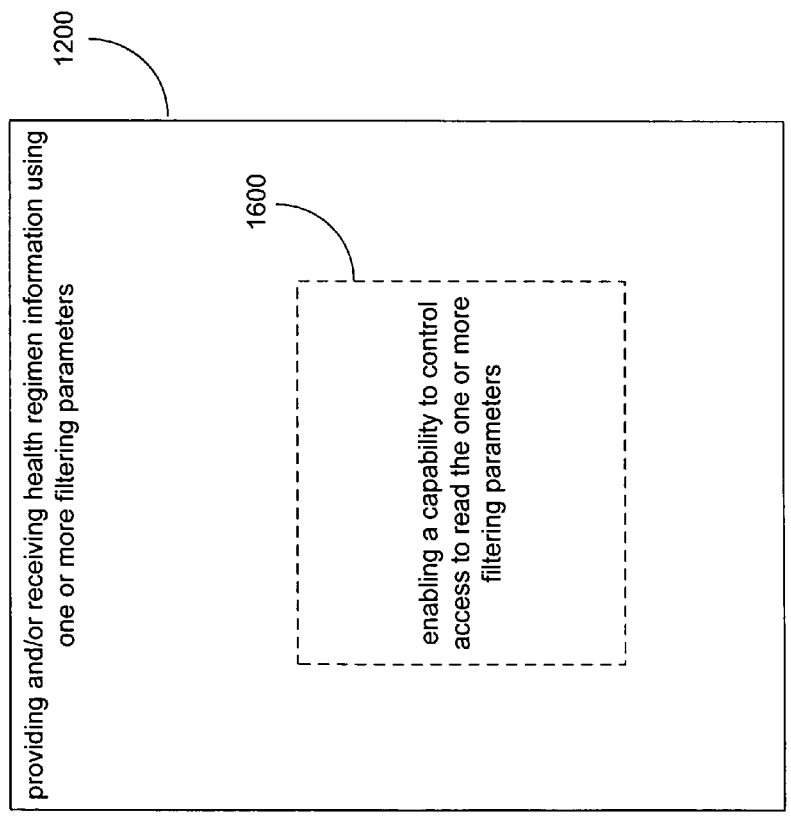
FIG. 16 illustrates an alternative implementation of the high-level logic flowchart of FIG. 12

FIG. 16 illustrates an alternative implementation of the high-level logic flowchart of FIG. 12. The depicted operational process may include operation 1200 and/or operation 1600. Operation 1200 is described in conjunction with FIG. 12. Operation 1200 and operation 1600 may be performed in any order and/or at least in part in parallel. Operation 1600 illustrates enabling a capability to control access to read the one or more filtering parameters (e.g., enabling a capability to control access to read the one or more filtering parameters, where an end-user interface device 104 and/or vendor interface device 114 and/or publisher interface device 122 and end-user logic 106 and/or vendor logic 116 and/or publisher logic 124 enable a capability for the end-user 102 and/or vendor 112 and/or publisher 120 to designate one or more persons or entities who may read the one or more filtering parameters). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200 and then end-user interface device 104 and/or vendor interface device 114 and/or publisher interface device 122 and end-user logic 106 and/or vendor logic 116 and/or publisher logic 124 enabling a capability for the end-user 102 and/or vendor 112 and/or publisher 120 to designate one or more persons or entities who may read the one or more filtering parameters according to operation 1600. Another aspect includes, e.g., an end-user interface device 104 and/or vendor interface device 114 and/or publisher interface device 122 and end-user logic 106 and/or vendor logic 116 and/or publisher logic 124 enabling a capability for the end-user 102 and/or vendor 112 and/or publisher 120 to designate one or more persons or entities who may read the one or more filtering parameters according to operation 1600 and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 1600 as described herein, and as illustrated herein by the sequential examples and in other aspects for which examples are implicitly provided for the sake of clarity, may be performed at least in part in parallel.

Figure 17:
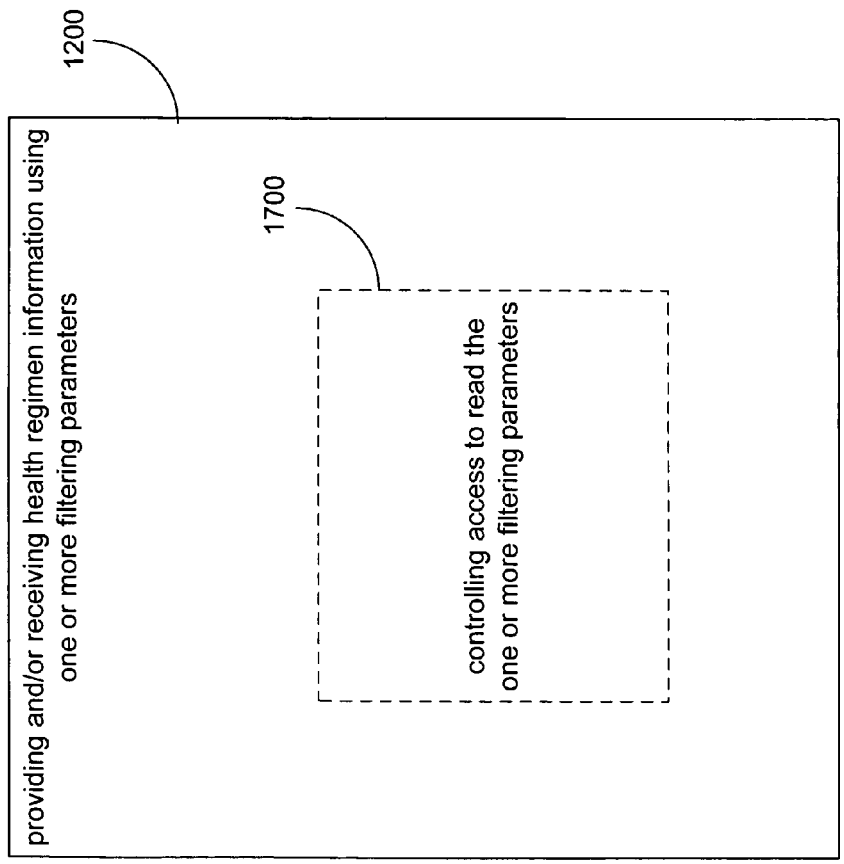
FIG. 17 depicts an alternative implementation of the high-level logic flowchart of FIG. 12

FIG. 17 depicts an alternative implementation of the high-level logic flowchart of FIG. 12. The depicted operational process may include operation 1200 and/or operation 1700. Operation 1200 is described in conjunction with FIG. 12. Operation 1200 and operation 1700 may be performed in any order and/or at least in part in parallel. Operation 1700 shows controlling access to read the one or more filtering parameters (e.g., controlling access to read the one or more filtering parameters, where an end-user interface device 104 and/or vendor interface device 114 and/or publisher interface device 122 and end-user logic 106 and/or vendor logic 116 and/or publisher logic 124 accepts and or denies access by the end-user 102 and/or vendor 112 and/or publisher 120 seeking to read the one or more filtering parameters). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200 and then end-user interface device 104 and/or vendor interface device 114 and/or publisher interface device 122 and end-user logic 106 and/or vendor logic 116 and/or publisher logic 124 controlling access to read the one or more filtering parameters by, e.g., accepting or denying access by the end-user 102 and/or vendor 112 and/or publisher 120 seeking to read the one or more filtering parameters according to operation 1700. Another aspect includes, e.g., an end-user interface device 104 and/or vendor interface device 114 and/or publisher interface device 122 and end-user logic 106 and/or vendor logic 116 and/or publisher logic 124 controlling access to read the one or more filtering parameters by, e.g., accepting or denying access by the end-user 102 and/or vendor 112 and/or publisher 120 seeking to read the one or more filtering parameters according to operation 1700 and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 1700 as described herein, and as illustrated herein by the sequential examples and in other aspects for which examples are implicitly provided for the sake of clarity, may be performed at least in part in parallel.

Figure 18:
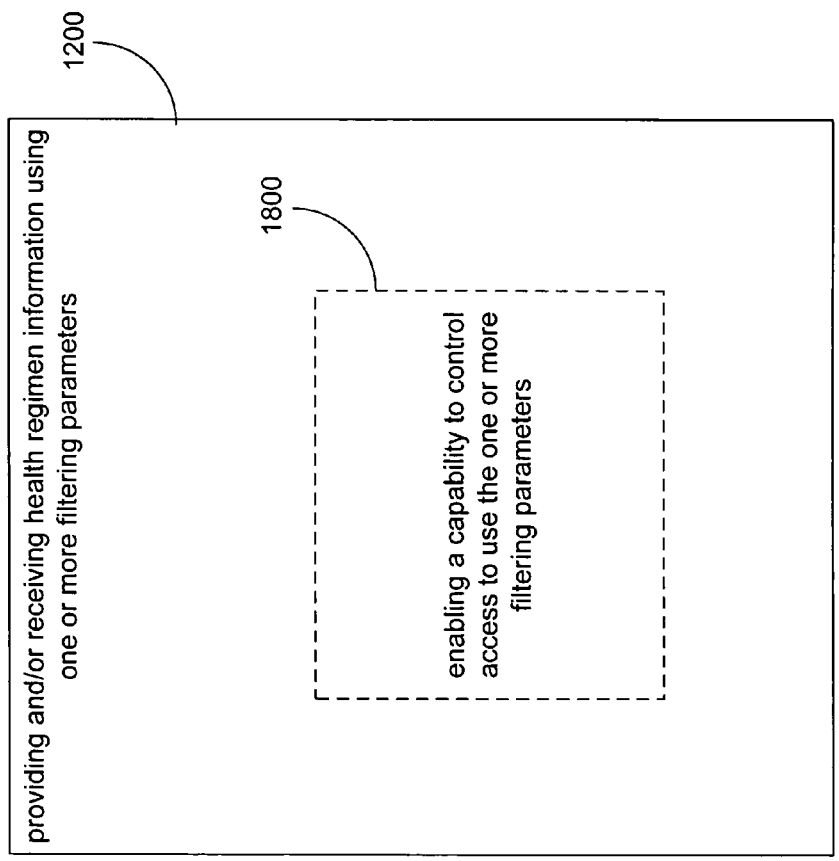
FIG. 18 shows an alternative implementation of the high-level logic flowchart of FIG. 12.

FIG. 18 shows an alternative implementation of the high-level logic flowchart of FIG. 12. The depicted operational process may include operation 1200 and/or operation 1800. Operation 1200 is described in conjunction with FIG. 12. Operation 1200 and operation 1800 may be performed in any order and/or at least in part in parallel. Operation 1800 depicts enabling a capability to control access to use the one or more filtering parameters (e.g., enabling a capability to control access to use the one or more filtering parameters, where an end-user interface device 104 and/or vendor interface device 114 and/or publisher interface device 122 and end-user logic 106 and/or vendor logic 116 and/or publisher logic 124 enable a capability to select a person and/or entity who may use the one or more filtering parameters to select health regimen information to be provided or received for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200 and then end-user interface device 104 and/or vendor interface device 114 and/or publisher interface device 122 and end-user logic 106 and/or vendor logic 116 and/or publisher logic 124 enabling a capability to control access to use the one or more filtering parameters by, e.g., enabling a capability to select a person and/or entity who may use the one or more filtering parameters to select health regimen information to be provided or received for/from the end-user 102 and/or vendor 112 and/or publisher 120. Another aspect includes, e.g., an end-user interface device 104 and/or vendor interface device 114 and/or publisher interface device 122 and end-user logic 106 and/or vendor logic 116 and/or publisher logic 124 enabling a capability to control access to use the one or more filtering parameters by, e.g., enabling a capability to select a person and/or entity who may use the one or more filtering parameters to select health regimen information to be provided or received for/from the end-user 102 and/or vendor 112 and/or publisher 120 according to operation 1800, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 1800 as described herein, and as illustrated herein by the sequential examples and in other aspects for which examples are implicitly provided for the sake of clarity, may be performed at least in part in parallel.

Figure 19:
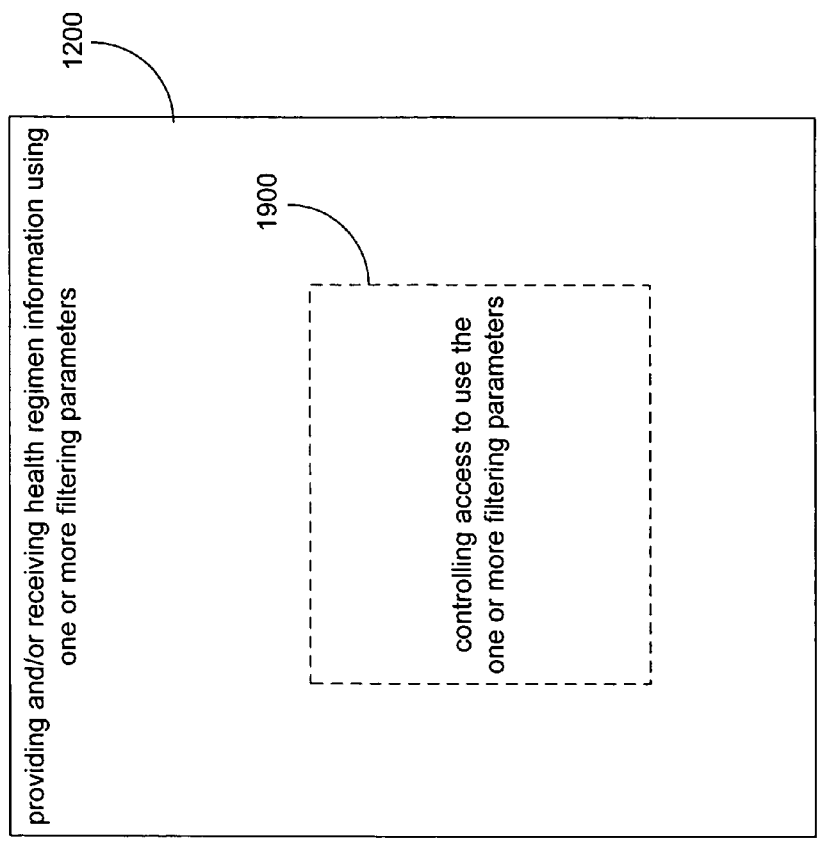
FIG. 19 illustrates an alternative implementation of the high-level logic flowchart of FIG. 12.

FIG. 19 illustrates an alternative implementation of the high-level logic flowchart of FIG. 12. The depicted operational process may include operation 1200 and/or operation 1900. Operation 1200 is described in conjunction with FIG. 12. Operation 1200 and operation 1900 may be performed in any order and/or at least in part in parallel. Operation 1900 depicts controlling access to use the one or more filtering parameters (e.g., controlling access to use the one or more filtering parameters, where an end-user interface device 104 and/or vendor interface device 114 and/or publisher interface device 122 and end-user logic 106 and/or vendor logic 116 and/or publisher logic 124 control which person and/or entity may use the one or more filtering parameters to select health regimen information to be provided and/or received for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 controlling access to use the one or more filtering parameters by, e.g., controlling which person and/or entity may use the one or more filtering parameters to select health regimen information to be provided and/or received for/from the end-user 102 and/or vendor 112 and/or publisher 120 according to operation 1900. Another aspect includes, e.g., an end-user interface device 104 and/or vendor interface device 114 and/or publisher interface device 122 and end-user logic 106 and/or vendor logic 116 and/or publisher logic 124 controlling access to use the one or more filtering parameters by, e.g., controlling which person and/or entity may use the one or more filtering parameters to select health regimen information to be provided and/or received for/from the end-user 102 and/or vendor 112 and/or publisher 120 according to operation 1900, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 1900 as described herein, and as illustrated herein by the sequential examples and in other aspects for which examples are implicitly provided for the sake of clarity, may be performed at least in part in parallel.

Figure 20:
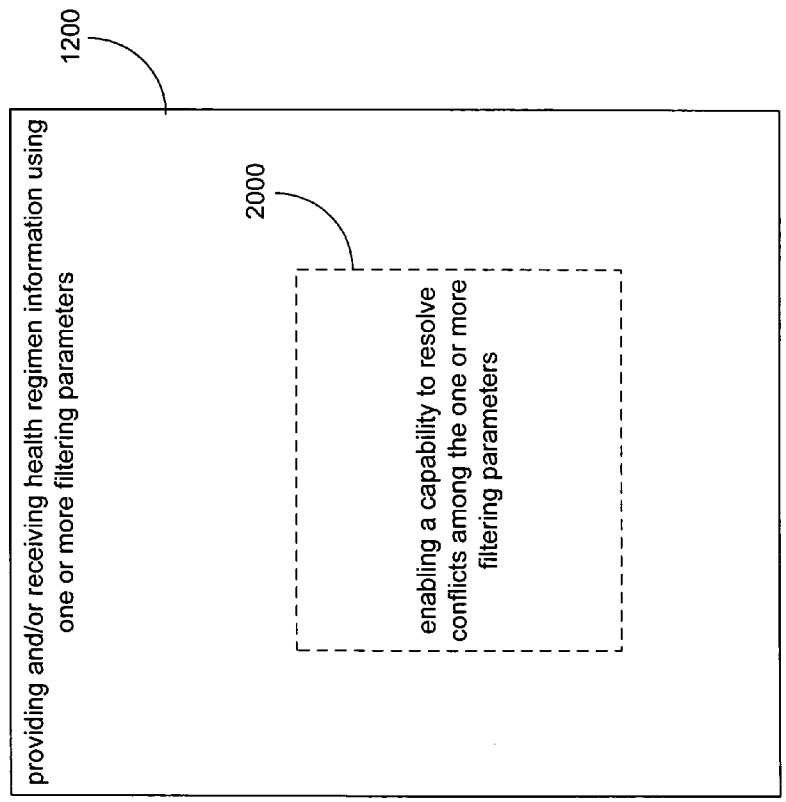
FIG. 20 illustrates an alternative implementation of the high-level logic flowchart of FIG. 12.

FIG. 20 illustrates an alternative implementation of the high-level logic flowchart of FIG. 12. The depicted operational process may include operation 1200 and/or operation 2000. Operation 1200 is described in conjunction with FIG. 12. Operation 1200 and operation 2000 may be performed in any order and/or at least in part in parallel. Operation 2000 illustrates enabling a capability to resolve conflicts among the one or more filtering parameters (e.g., enabling a capability to resolve conflicts among the one or more filtering parameters, where an end-user interface device 104 and/or vendor interface device 114 and/or publisher interface device 122 and end-user logic 106 and/or vendor logic 116 and/or publisher logic 124 enable a capability for the end-user 102 and/or vendor 112 and/or publisher 120 to select the use of one filtering parameter over the use of another filtering parameter where the use of both filtering parameters is mutually exclusive). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 enabling a capability to resolve conflicts among the one or more filtering parameters by, e.g., enabling a capability for the end-user 102 and/or vendor 112 and/or publisher 120 to select the use of one filtering parameter over the use of another filtering parameter where the use of both filtering parameters is mutually exclusive according to operation 2000. Another aspect includes, e.g., an end-user interface device 104 and/or vendor interface device 114 and/or publisher interface device 122 and end-user logic 106 and/or vendor logic 116 and/or publisher logic 124 enabling a capability to resolve conflicts among the one or more filtering parameters by, e.g., enabling a capability for the end-user 102 and/or vendor 112 and/or publisher 120 to select the use of one filtering parameter over the use of another filtering parameter where the use of both filtering parameters is mutually exclusive according to operation 2000, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2000 as described herein, and as illustrated herein by the sequential examples and in other aspects for which examples are implicitly provided for the sake of clarity, may be performed at least in part in parallel.

Figure 21:
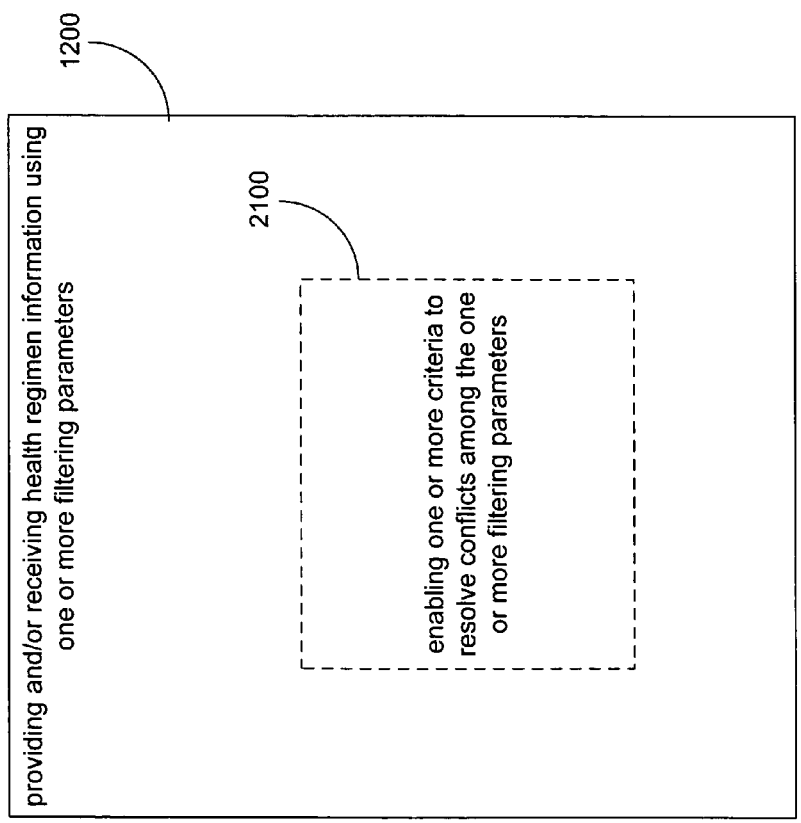
FIG. 21 depicts an alternative implementation of the high-level logic flowchart of FIG. 12.

FIG. 21 depicts an alternative implementation of the high-level logic flowchart of FIG. 12. The depicted operational process may include operation 1200 and/or operation 2100. Operation 1200 is described in conjunction with FIG. 12. Operation 1200 and operation 2100 may be performed in any order and/or at least in part in parallel. Operation 2100 shows enabling one or more criteria to resolve conflicts among the one or more filtering parameters (e.g., enabling one or more criteria to resolve conflicts among the one or more filtering parameters, where an end-user interface device 104 and/or vendor interface device 114 and/or publisher interface device 122 and end-user logic 106 and/or vendor logic 116 and/or publisher logic 124 enable a predetermined preference of the end-user 102 and/or vendor 112 and/or publisher 120 for the use of one filtering parameter over the use of another filtering parameter where the use of both filtering parameters is mutually exclusive). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 enabling one or more criteria to resolve conflicts among the one or more filtering parameters by, e.g., enabling a predetermined preference of the end-user 102 and/or vendor 112 and/or publisher 120 for the use of one filtering parameter over the use of another filtering parameter where the use of both filtering parameters is mutually exclusive according to operation 2100. Another aspect includes, e.g., an end-user interface device 104 and/or vendor interface device 114 and/or publisher interface device 122 and end-user logic 106 and/or vendor logic 116 and/or publisher logic 124 enabling one or more criteria to resolve conflicts among the one or more filtering parameters by, e.g., enabling a predetermined preference of the end-user 102 and/or vendor 112 and/or publisher 120 for the use of one filtering parameter over the use of another filtering parameter where the use of both filtering parameters is mutually exclusive according to operation 2100, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2100 as described herein, and as illustrated herein by the sequential examples and in other aspects for which examples are implicitly provided for the sake of clarity, may be performed at least in part in parallel.

Figure 22:
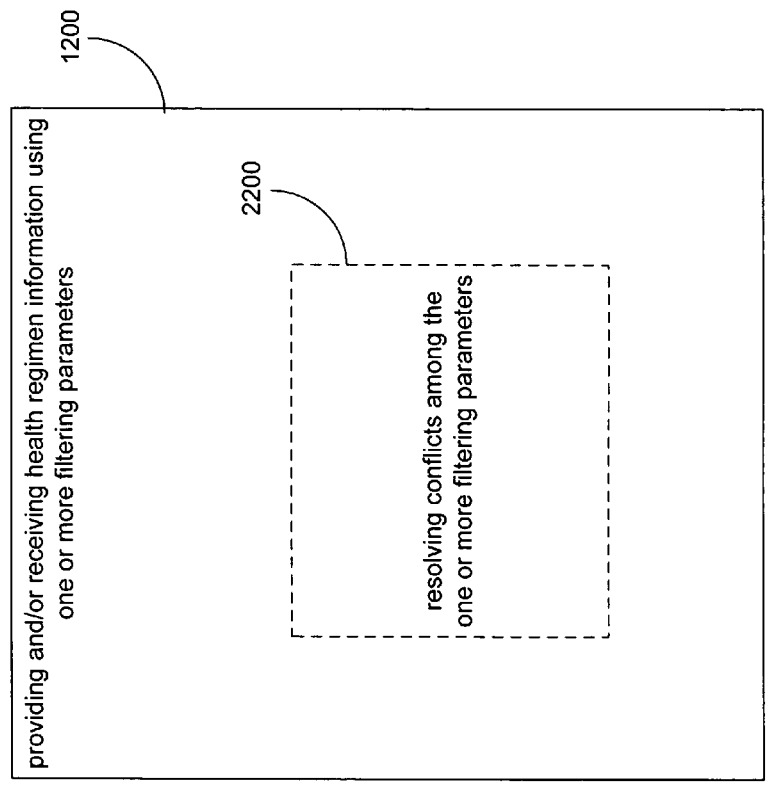
FIG. 22 shows an alternative implementation of the high-level logic flowchart of FIG. 12.

FIG. 22 shows an alternative implementation of the high-level logic flowchart of FIG. 12. The depicted operational process may include operation 1200 and/or operation 2200. Operation 1200 is described in conjunction with FIG. 12. Operation 1200 and operation 2200 may be performed in any order and/or at least in part in parallel. Operation 2200 depicts resolving conflicts among the one or more filtering parameters (e.g., resolving conflicts among the one or more filtering parameters, where an end-user interface device 104 and/or vendor interface device 114 and/or publisher interface device 122 and end-user logic 106 and/or vendor logic 116 and/or publisher logic 124 use a predetermined preference of the end-user 102 and/or vendor 112 and/or publisher 120 for the use of one filtering parameter over the use of another filtering parameter where the use of both filtering parameters is mutually exclusive). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 resolving conflicts among the one or more filtering parameters by, e.g., using a predetermined preference of the end-user 102 and/or vendor 112 and/or publisher 120 for the use of one filtering parameter over the use of another filtering parameter where the use of both filtering parameters is mutually exclusive according to operation 2200. Another aspect includes, e.g., an end-user interface device 104 and/or vendor interface device 114 and/or publisher interface device 122 and end-user logic 106 and/or vendor logic 116 and/or publisher logic 124 resolving conflicts among the one or more filtering parameters by, e.g., using a predetermined preference of the end-user 102 and/or vendor 112 and/or publisher 120 for the use of one filtering parameter over the use of another filtering parameter where the use of both filtering parameters is mutually exclusive according to operation 2200, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2200 as described herein, and as illustrated herein by the sequential examples and in other aspects for which examples are implicitly provided for the sake of clarity, may be performed at least in part in parallel.

Figure 23:
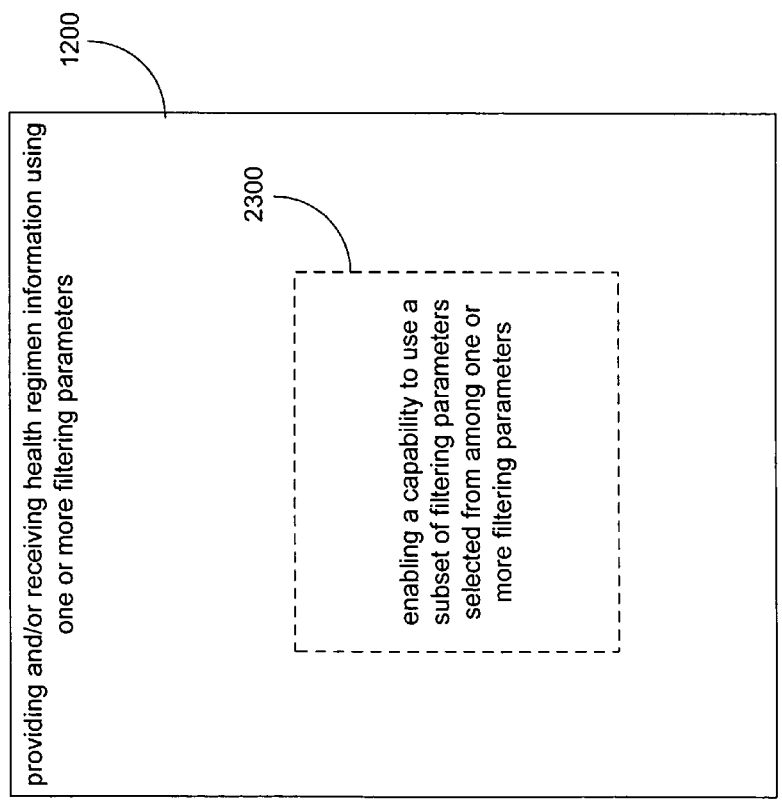
FIG. 23 depicts an alternative implementation of the high-level logic flowchart of FIG. 12.

FIG. 23 depicts an alternative implementation of the high-level logic flowchart of FIG. 12. The depicted operational process may include operation 1200 and/or operation 2300. Operation 1200 is described in conjunction with FIG. 12. Operation 1200 and operation 2300 may be performed in any order and/or at least in part in parallel. Operation 2300 shows enabling a capability to use a subset of filtering parameters selected from among one or more filtering parameters (e.g., enabling a capability to use a subset of filtering parameters selected from among one or more filtering parameters, where an end-user interface device 104 and/or vendor interface device 114 and/or publisher interface device 122 and end-user logic 106 and/or vendor logic 116 and/or publisher logic 124 enable a capability to use three of five predetermined filtering parameters to provide and/or receive health regimen information for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 enabling a capability to use a subset of filtering parameters selected from among one or more filtering parameters by, e.g., enabling a capability to use three of five predetermined filtering parameters to provide and/or receive health regimen information for/from the end-user 102 and/or vendor 112 and/or publisher 120 according to operation 2300. Another aspect includes, e.g., an end-user interface device 104 and/or vendor interface device 114 and/or publisher interface device 122 and end-user logic 106 and/or vendor logic 116 and/or publisher logic 124 enabling a capability to use a subset of filtering parameters selected from among one or more filtering parameters by, e.g., enabling a capability to use three of five predetermined filtering parameters to provide and/or receive health regimen information for/from the end-user 102 and/or vendor 112 and/or publisher 120 according to operation 2300, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2300 as described herein, and as illustrated herein by the sequential examples and in other aspects for which examples are implicitly provided for the sake of clarity, may be performed at least in part in parallel.

Figure 24:
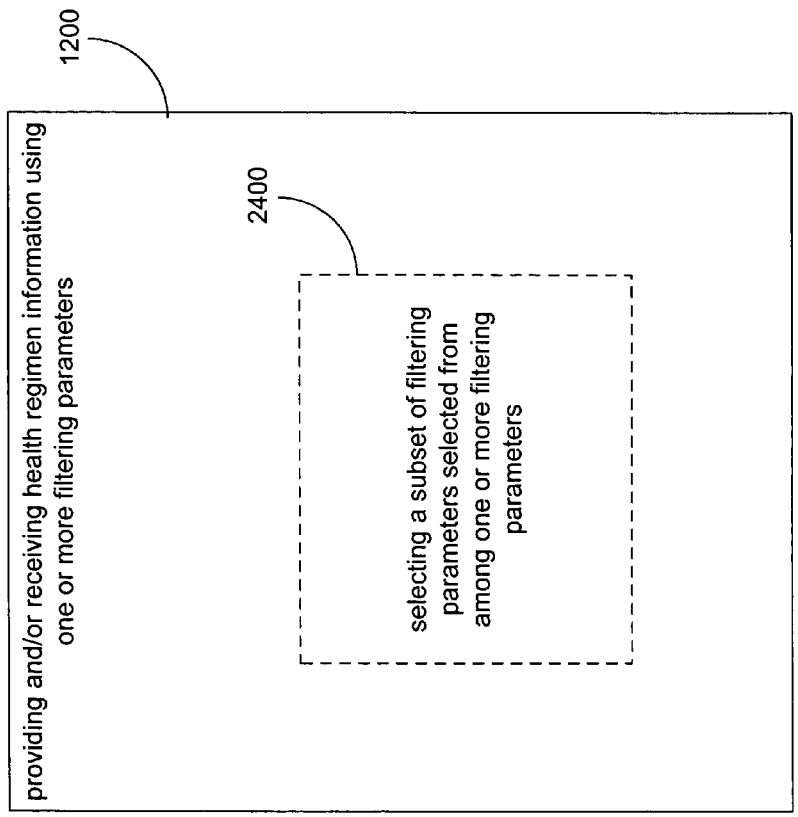
FIG. 24 shows an alternative implementation of the high-level logic flowchart of FIG. 12.

FIG. 24 shows an alternative implementation of the high-level logic flowchart of FIG. 12. The depicted operational process may include operation 1200 and/or operation 2400. Operation 1200 is described in conjunction with FIG. 12. Operation 1200 and operation 2400 may be performed in any order and/or at least in part in parallel. Operation 2400 shows selecting a subset of filtering parameters selected from among one or more filtering parameters (e.g., selecting a subset of filtering parameters selected from among one or more filtering parameters, where an end-user interface device 104 and/or vendor interface device 114 and/or publisher interface device 122 and end-user logic 106 and/or vendor logic 116 and/or publisher logic 124 use predetermined criteria to select three of five predetermined filtering parameters to provide and/or receive health regimen information for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 selecting a subset of filtering parameters selected from among one or more filtering parameters by, e.g., using predetermined criteria to select three of five predetermined filtering parameters to provide and/or receive health regimen information for/from the end-user 102 and/or vendor 112 and/or publisher 120 according to operation 2400. Another aspect includes, e.g., an end-user interface device 104 and/or vendor interface device 114 and/or publisher interface device 122 and end-user logic 106 and/or vendor logic 116 and/or publisher logic 124 selecting a subset of filtering parameters selected from among one or more filtering parameters by, e.g., using predetermined criteria to select three of five predetermined filtering parameters to provide and/or receive health regimen information for/from the end-user 102 and/or vendor 112 and/or publisher 120 according to operation 2400, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2400 as described herein, and as illustrated herein by the sequential examples and in other aspects for which examples are implicitly provided for the sake of clarity, may be performed at least in part in parallel.

Figure 25:
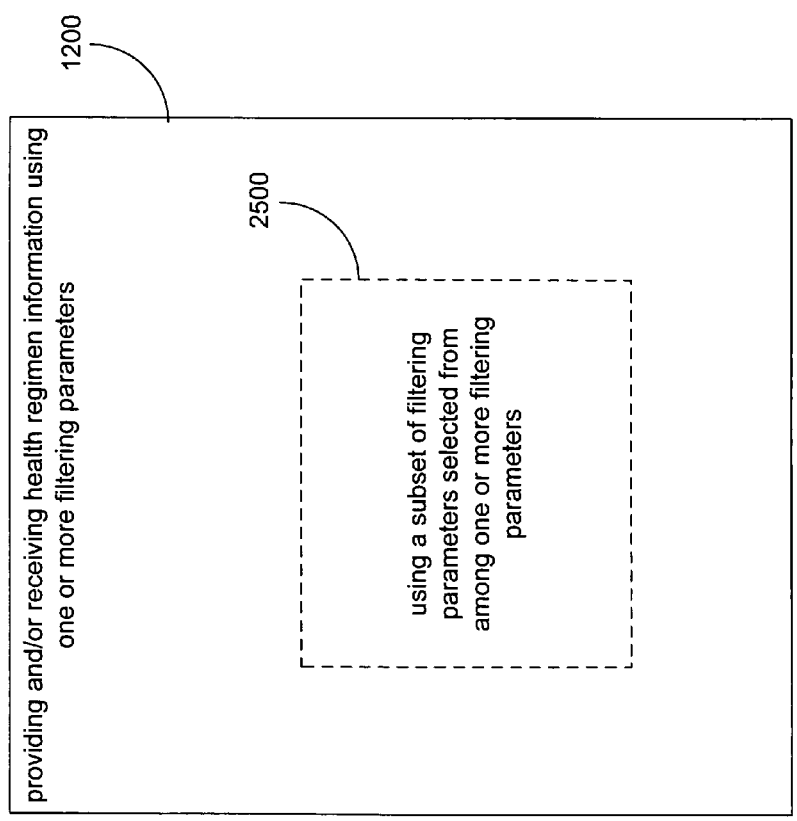
FIG. 25 illustrates an alternative implementation of the high-level logic flowchart of FIG. 12.

FIG. 25 illustrates an alternative implementation of the high-level logic flowchart of FIG. 12. The depicted operational process may include operation 1200 and/or operation 2500. Operation 1200 is described in conjunction with FIG. 12. Operation 1200 and operation 2500 may be performed in any order and/or at least in part in parallel. Operation 2500 illustrates using a subset of filtering parameters selected from among one or more filtering parameters (e.g., using a subset of filtering parameters selected from among one or more filtering parameters, where an end-user interface device 104 and/or vendor interface device 114 and/or publisher interface device 122 and end-user logic 106 and/or vendor logic 116 and/or publisher logic 124 use three of five predetermined filtering parameters to provide and/or receive health regimen information for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 using a subset of filtering parameters selected from among one or more filtering parameters by, e.g., using three of five predetermined filtering parameters to provide and/or receive health regimen information for/from the end-user 102 and/or vendor 112 and/or publisher 120 according to operation 2500. Another aspect includes, e.g., an end-user interface device 104 and/or vendor interface device 114 and/or publisher interface device 122 and end-user logic 106 and/or vendor logic 116 and/or publisher logic 124 using a subset of filtering parameters selected from among one or more filtering parameters by, e.g., using three of five predetermined filtering parameters to provide and/or receive health regimen information for/from the end-user 102 and/or vendor 112 and/or publisher 120 according to operation 2500, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2500 as described herein, and as illustrated herein by the sequential examples and in other aspects for which examples are implicitly provided for the sake of clarity, may be performed at least in part in parallel.

Figure 26:
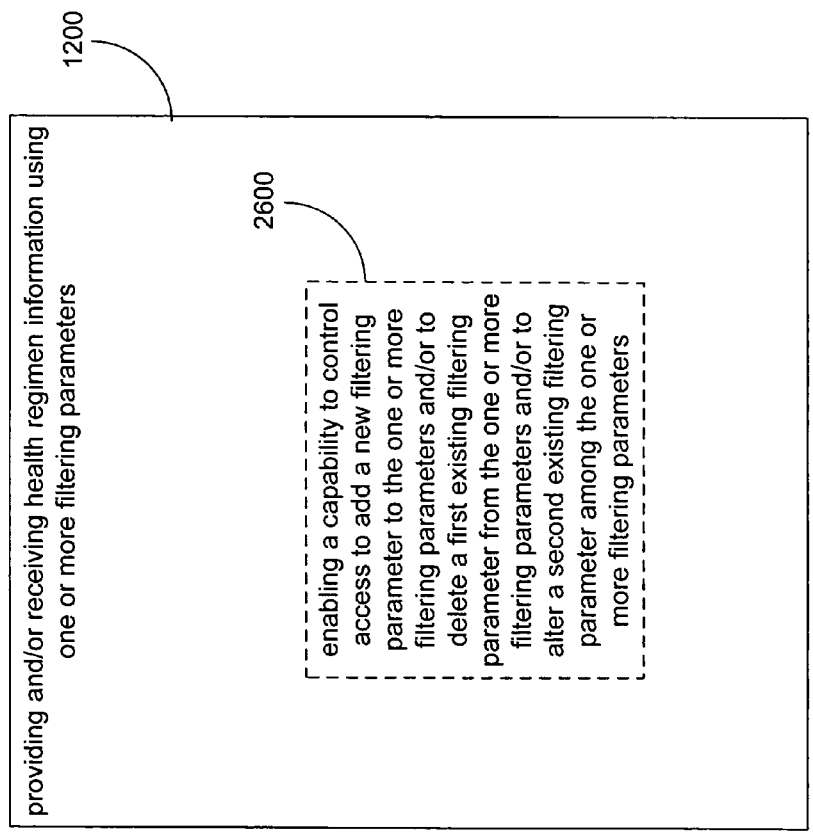
FIG. 26 depicts an alternative implementation of the high-level logic flowchart of FIG. 12.

FIG. 26 depicts an alternative implementation of the high-level logic flowchart of FIG. 12. The depicted operational process may include operation 1200 and/or operation 2600. Operation 1200 is described in conjunction with FIG. 12. Operation 1200 and operation 2600 may be performed in any order and/or at least in part in parallel. Operation 2600 shows enabling a capability to control access to add a new filtering parameter to the one or more filtering parameters and/or to delete a first existing filtering parameter from the one or more filtering parameters and/or to alter a second existing filtering parameter among the one or more filtering parameters (e.g., enabling a capability to control access to add a new filtering parameter to the one or more filtering parameters and/or to delete a first existing filtering parameter from the one or more filtering parameters and/or to alter a second existing filtering parameter among the one or more filtering parameters, where an end-user interface device 104 and/or vendor interface device 114 and/or publisher interface device 122 and end-user logic 106 and/or vendor logic 116 and/or publisher logic 124 enable a capability to permit and/or deny persons and/or entities who may add to, delete from, and/or alter a set of filtering parameters to be used to provide and/or receive health regimen information for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 enabling a capability to control access to add a new filtering parameter to the one or more filtering parameters and/or to delete a first existing filtering parameter from the one or more filtering parameters and/or to alter a second existing filtering parameter among the one or more filtering parameters by e.g., enabling a capability to permit and/or deny persons and/or entities who may add to, delete from, and/or alter a set of filtering parameters to be used to provide and/or receive health regimen information for/from the end-user 102 and/or vendor 112 and/or publisher 120 according to operation 2600. Another aspect includes, e.g., an end-user interface device 104 and/or vendor interface device 114 and/or publisher interface device 122 and end-user logic 106 and/or vendor logic 116 and/or publisher logic 124 enabling a capability to control access to add a new filtering parameter to the one or more filtering parameters and/or to delete a first existing filtering parameter from the one or more filtering parameters and/or to alter a second existing filtering parameter among the one or more filtering parameters by e.g., enabling a capability to permit and/or deny persons and/or entities who may add to, delete from, and/or alter a set of filtering parameters to be used to provide and/or receive health regimen information for/from the end-user 102 and/or vendor 112 and/or publisher 120 according to operation 2600, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2600 as described herein, and as illustrated herein by the sequential examples and in other aspects for which examples are implicitly provided for the sake of clarity, may be performed at least in part in parallel.

Figure 27:
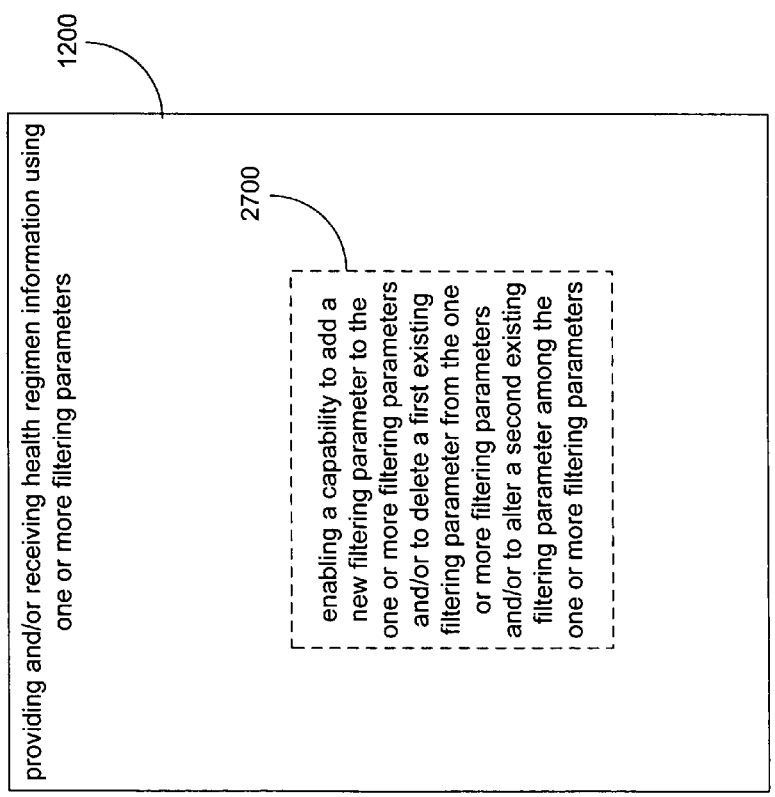
FIG. 27 shows an alternative implementation of the high-level logic flowchart of FIG. 12.

FIG. 27 shows an alternative implementation of the high-level logic flowchart of FIG. 12. The depicted operational process may include operation 1200 and/or operation 2700. Operation 1200 is described in conjunction with FIG. 12. Operation 1200 and operation 2700 may be performed in any order and/or at least in part in parallel. Operation 2700 depicts enabling a capability to add a new filtering parameter to the one or more filtering parameters and/or to delete a first existing filtering parameter from the one or more filtering parameters and/or to alter a second existing filtering parameter among the one or more filtering parameters (e.g., enabling a capability to add a new filtering parameter to the one or more filtering parameters and/or to delete a first existing filtering parameter from the one or more filtering parameters and/or to alter a second existing filtering parameter among the one or more filtering parameters, where an end-user interface device 104 and/or vendor interface device 114 and/or publisher interface device 122 and end-user logic 106 and/or vendor logic 116 and/or publisher logic 124 enable a capability to persons and/or entities to add to, delete from, and/or alter a set of filtering parameters to be used to provide and/or receive health regimen information for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 enabling a capability to add a new filtering parameter to the one or more filtering parameters and/or to delete a first existing filtering parameter from the one or more filtering parameters and/or to alter a second existing filtering parameter among the one or more filtering parameters by, e.g., enabling a capability to persons and/or entities to add to, delete from, and/or alter a set of filtering parameters to be used to provide and/or receive health regimen information for/from the end-user 102 and/or vendor 112 and/or publisher 120 according to operation 2700. Another aspect includes, e.g., an end-user interface device 104 and/or vendor interface device 114 and/or publisher interface device 122 and end-user logic 106 and/or vendor logic 116 and/or publisher logic 124 enabling a capability to add a new filtering parameter to the one or more filtering parameters and/or to delete a first existing filtering parameter from the one or more filtering parameters and/or to alter a second existing filtering parameter among the one or more filtering parameters by, e.g., enabling a capability to persons and/or entities to add to, delete from, and/or alter a set of filtering parameters to be used to provide and/or receive health regimen information for/from the end-user 102 and/or vendor 112 and/or publisher 120 according to operation 2700, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2700 as described herein, and as illustrated herein by the sequential examples and in other aspects for which examples are implicitly provided for the sake of clarity, may be performed at least in part in parallel.

Figure 28:
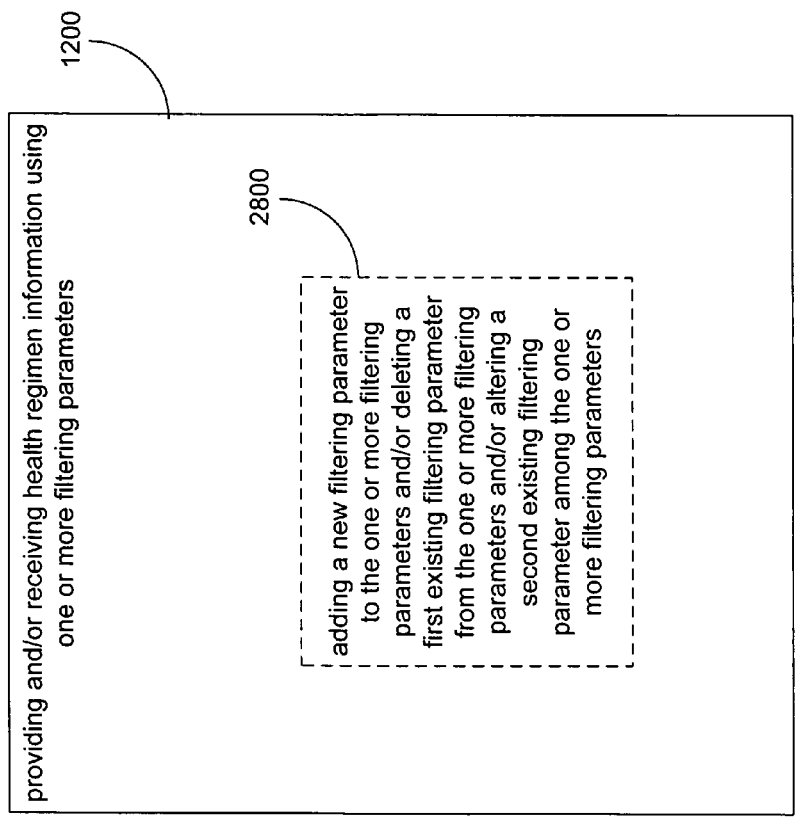
FIG. 28 depicts an alternative implementation of the high-level logic flowchart of FIG. 12.

FIG. 28 depicts an alternative implementation of the high-level logic flowchart of FIG. 12. The depicted operational process may include operation 1200 and/or operation 2800. Operation 1200 is described in conjunction with FIG. 12. Operation 1200 and operation 2800 may be performed in any order and/or at least in part in parallel. Operation 2800 illustrates adding a new filtering parameter to the one or more filtering parameters and/or deleting a first existing filtering parameter from the one or more filtering parameters and/or altering a second existing filtering parameter among the one or more filtering parameters (e.g., adding a new filtering parameter to the one or more filtering parameters and/or deleting a first existing filtering parameter from the one or more filtering parameters and/or altering a second existing filtering parameter among the one or more filtering parameters, where an end-user interface device 104 and/or vendor interface device 114 and/or publisher interface device 122 and end-user logic 106 and/or vendor logic 116 and/or publisher logic 124 accepts input to add to, delete from, and/or alter a set of filtering parameters to be used to provide and/or receive health regimen information for/from the end-user 102 and/or vendor 112 and/or publisher 120). One aspect includes, e.g., an end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200, and then end-user interface device 104 and/or vendor interface device 114 and/or publisher interface device 122 and end-user logic 106 and/or vendor logic 116 and/or publisher logic 124 adding a new filtering parameter to the one or more filtering parameters and/or deleting a first existing filtering parameter from the one or more filtering parameters and/or altering a second existing filtering parameter among the one or more filtering parameters by, e.g., accepting input to add to, delete from, and/or alter a set of filtering parameters to be used to provide and/or receive health regimen information for/from the end-user 102 and/or vendor 112 and/or publisher 120 according to operation 2800. Another aspect includes, e.g., an end-user interface device 104 and/or vendor interface device 114 and/or publisher interface device 122 and end-user logic 106 and/or vendor logic 116 and/or publisher logic 124 adding a new filtering parameter to the one or more filtering parameters and/or deleting a first existing filtering parameter from the one or more filtering parameters and/or altering a second existing filtering parameter among the one or more filtering parameters by, e.g., accepting input to add to, delete from, and/or alter a set of filtering parameters to be used to provide and/or receive health regimen information for/from the end-user 102 and/or vendor 112 and/or publisher 120 according to operation 2800, and then end-user interface device 104 and/or vendor interface device 114 and/or publisher interface device 122 and end-user logic 106 and/or vendor logic 116 and/or publisher logic 124 providing and/or receiving health regimen information using one or more filtering parameters according to operation 1200. Those skilled in the art will appreciate that operations 1200 and 2800 as described herein, and as illustrated herein by the sequential examples and in other aspects for which examples are implicitly provided for the sake of clarity, may be performed at least in part in parallel.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. Patens, U.S. patent application publications, U.S. patent applications, foreign patents, foreign patent applications and non-patent publications referred to in this specification and/or listed in any Application Data Sheet, are incorporated herein by reference, in their entireties.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

We claim:

1. A system comprising:
    circuitry configured for obtaining at least one filtering parameter concerning at least one physical appearance characteristic of at least one genetically-related family member of a user;
    circuitry configured for inferring at least one genetic profile of at least one of the user or the at least one genetically-related family member of the user based at least partly on the at least one filtering parameter concerning the at least one physical appearance characteristic of the at least one genetically-related family member of the user; and
    circuitry configured for selecting at least one health regimen including at least one or more dietary supplements for the user based at least partly on the at least one genetic profile of at least one of the user or the at least one genetically-related family member of the user.

2. The system of claim 1, wherein the circuitry configured for obtaining at least one filtering parameter concerning at least one physical appearance characteristic of at least one genetically-related family member of a user comprises:
    circuitry configured for obtaining from storage at least one filtering parameter concerning at least one physical appearance characteristic of at least one genetically-related family member of a user.

3. The system of claim 1, wherein the circuitry configured for obtaining at least one filtering parameter concerning at least one physical appearance characteristic of at least one genetically-related family member of a user comprises:
    circuitry configured for obtaining user input of at least one filtering parameter concerning at least one physical appearance characteristic of at least one genetically-related family member of a user.

4. The system of claim 1, wherein the circuitry configured for obtaining at least one filtering parameter concerning at least one physical appearance characteristic of at least one genetically-related family member of a user comprises:
    circuitry configured for obtaining at least one first filtering parameter concerning at least one physiological characteristic and at least one second filtering parameter concerning at least one physical appearance characteristic of at least one genetically-related family member of a user.

5. The system of claim 1, wherein the circuitry configured for obtaining at least one filtering parameter concerning at least one physical appearance characteristic of at least one genetically-related family member of a user comprises:
    circuitry configured for obtaining at least one first filtering parameter concerning at least one psychological characteristic and at least one second filtering parameter concerning at least one physical appearance characteristic of at least one genetically-related family member of a user.

6. The system of claim 1, wherein the circuitry configured for obtaining at least one filtering parameter concerning at least one physical appearance characteristic of at least one genetically-related family member of a user comprises:
    circuitry configured for obtaining at least one filtering parameter concerning at least one objective physical appearance characteristic of at least one genetically-related family member of a user.

7. The system of claim 1, wherein the circuitry configured for obtaining at least one filtering parameter concerning at least one physical appearance characteristic of at least one genetically-related family member of a user comprises:
    circuitry configured for obtaining at least one filtering parameter concerning at least one subjective physical appearance characteristic of at least one genetically-related family member of a user.

8. The system of claim 1, wherein the circuitry configured for inferring at least one genetic profile of at least one of the user or the at least one genetically-related family member of the user based at least partly on the at least one filtering parameter concerning the at least one physical appearance characteristic of the at least one genetically-related family member of the user comprises:

circuitry configured for inferring at least one genetic profile of the user and the at least one genetically-related family member of the user based at least partly on the at least one filtering parameter concerning the at least one physical appearance characteristic of the at least one genetically-related family member of the user.

9. The system of claim 1, wherein the circuitry configured for inferring at least one genetic profile of at least one of the user or the at least one genetically-related family member of the user based at least partly on the at least one filtering parameter concerning the at least one physical appearance characteristic of the at least one genetically-related family member of the user comprises:

circuitry configured for inferring at least one genetic signature of at least one of the user or the at least one genetically-related family member of the user based at least partly on the at least one filtering parameter concerning the at least one physical appearance characteristic of the at least one genetically-related family member of the user.

10. The system of claim 1, wherein the circuitry configured for inferring at least one genetic profile of at least one of the user or the at least one genetically-related family member of the user based at least partly on the at least one filtering parameter concerning the at least one physical appearance characteristic of the at least one genetically-related family member of the user comprises:

circuitry configured for inferring at least one genetic disequilibrium of at least one of the user or the at least one genetically-related family member of the user based at least partly on the at least one filtering parameter concerning the at least one physical appearance characteristic of the at least one genetically-related family member of the user.

11. The system of claim 1, wherein the circuitry configured for inferring at least one genetic profile of at least one of the user or the at least one genetically-related family member of the user based at least partly on the at least one filtering parameter concerning the at least one physical appearance characteristic of the at least one genetically-related family member of the user comprises:

circuitry configured for inferring at least one genetic characteristic of at least one of the user or the at least one genetically-related family member of the user based at least partly on the at least one filtering parameter concerning the at least one physical appearance characteristic of the at least one genetically-related family member of the user.

12. The system of claim 1, wherein the circuitry configured for selecting at least one health regimen including at least one or more dietary supplements for the user based at least partly on the at least one genetic profile of at least one of the user or the at least one genetically-related family member of the user comprises:

circuitry configured for selecting at least one health regimen including at least one or more dietary supplements to address at least one physical appearance characteristic of the user based at least partly on the at least one genetic profile of at least one of the user or the at least one genetically-related family member of the user.

13. The system of claim 1, wherein the circuitry configured for selecting at least one health regimen including at least one or more dietary supplements for the user based at least partly on the at least one genetic profile of at least one of the user or the at least one genetically-related family member of the user comprises:

circuitry configured for selecting at least one health regimen including at least one or more dietary supplements to address at least one physiological aspect of the user based at least partly on the at least one genetic profile of at least one of the user or the at least one genetically-related family member of the user.

14. The system of claim 1, wherein the circuitry configured for selecting at least one health regimen including at least one or more dietary supplements for the user based at least partly on the at least one genetic profile of at least one of the user or the at least one genetically-related family member of the user comprises:

circuitry configured for selecting at least one health regimen including at least one or more dietary supplements to address at least one psychological aspect of the user based at least partly on the at least one genetic profile of at least one of the user or the at least one genetically-related family member of the user.

15. The system of claim 1, wherein the circuitry configured for selecting at least one health regimen including at least one or more dietary supplements for the user based at least partly on the at least one genetic profile of at least one of the user or the at least one genetically-related family member of the user comprises:

circuitry configured for selecting at least one health regimen including at least one or more of the following types of dietary supplements: drug, electrolyte, vitamin, and/or nutraceutical.

16. The system of claim 1, wherein the circuitry configured for selecting at least one health regimen including at least one or more dietary supplements for the user based at least partly on the at least one genetic profile of at least one of the user or the at least one genetically-related family member of the user comprises:

circuitry configured for selecting at least one health regimen including at least one or more dietary supplements for the user based at least partly on the at least one genetic profile of the user and the at least one genetically-related family member of the user.

17. The system of claim 1, wherein the circuitry configured for selecting at least one health regimen including at least one or more dietary supplements for the user based at least partly on the at least one genetic profile of at least one of the user or the at least one genetically-related family member of the user comprises:

circuitry configured for selecting at least one health regimen including at least one or more dietary supplements for the user based at least partly on (i) the at least one genetic profile of at least one of the user or the at least one genetically-related family member of the user and (ii) at least one diet feature of the user.

18. The system of claim 1, wherein the circuitry configured for selecting at least one health regimen including at least one or more dietary supplements for the user based at least partly on the at least one genetic profile of at least one of the user or the at least one genetically-related family member of the user comprises:

circuitry configured for selecting at least one health regimen including at least one or more dietary supplements for the user based at least partly on (i) the at least one genetic profile of at least one of the user or the at least one genetically-related family member of the user and (ii) at least one medical condition of the user.

19. The system of claim 1, wherein the circuitry configured for selecting at least one health regimen including at least one or more dietary supplements for the user based at least partly on the at least one genetic profile of at least one of the user or the at least one genetically-related family member of the user comprises:
   circuitry configured for selecting at least one health regimen including at least one or more dietary supplements for the user based at least partly on (i) the at least one genetic profile of at least one of the user or the at least one genetically-related family member of the user and (ii) physiological information associated with the user.

20. The system of claim 1, wherein the circuitry configured for selecting at least one health regimen including at least one or more dietary supplements for the user based at least partly on the at least one genetic profile of at least one of the user or the at least one genetically-related family member of the user comprises:
   circuitry configured for selecting at least one health regimen including at least one or more dietary supplements for the user based at least partly on (i) the at least one genetic profile of at least one of the user or the at least one genetically-related family member of the user and (ii) one or more of the following parameters: substance intake, substance to be excluded, current activity, anticipated activity, cost, regimen credibility, external condition, supplement availability, psychological condition, experiential result, anticipated geographic location, environmental condition, social indication, and/or homeostatic mechanism.

21. The system of claim 1, further comprising:
   circuitry configured for providing the at least one health regimen including at least one or more dietary supplements.

22. The system of claim 1, further comprising:
   circuitry configured for providing via at least one interface the at least one health regimen including at least one or more dietary supplements.

23. The system of claim 1, further comprising:
   circuitry configured for providing via at least one device the at least one health regimen including at least one or more dietary supplements.

24. The system of claim 1, further comprising:
   circuitry configured for providing via at least one network the at least one health regimen including at least one or more dietary supplements.

25. The system of claim 1, wherein the circuitry configured for obtaining at least one filtering parameter concerning at least one physical appearance characteristic of at least one genetically-related family member of a user comprises:
   circuitry configured for obtaining at least one filtering parameter concerning at least one of the following types of physical appearance characteristics of at least one genetically-related family member of a user: weight and/or hair loss.

26. The system of claim 1, wherein the circuitry configured for inferring at least one genetic profile of at least one of the user or the at least one genetically-related family member of the user based at least partly on the at least one filtering parameter concerning the at least one physical appearance characteristic of the at least one genetically-related family member of the user comprises:
   circuitry configured for inferring at least one genetic profile of at least one of the user or the at least one genetically-related family member of the user based at least partly on (i) the at least one filtering parameter concerning the at least one physical appearance characteristic of the at least one genetically-related family member of the user and (ii) at least one other filtering parameter concerning at least one other trait of the at least one genetically-related family member of the user.

27. A method comprising:
   obtaining at least one filtering parameter concerning at least one physical appearance characteristic of at least one genetically-related family member of a user;
   inferring, using one or more processors, at least one genetic profile of at least one of the user or the at least one genetically-related family member of the user based at least partly on the at least one filtering parameter concerning the at least one physical appearance characteristic of the at least one genetically-related family member of the user; and
   selecting at least one health regimen including at least one or more dietary supplements for the user based at least partly on the at least one genetic profile of at least one of the user or the at least one genetically-related family member of the user.

28. A computer program product comprising:
   one or more non-transitory media including at least:
   one or more instructions for obtaining at least one filtering parameter concerning at least one physical appearance characteristic of at least one genetically-related family member of a user;
   one or more instructions for inferring at least one genetic profile of at least one of the user or the at least one genetically-related family member of the user based at least partly on the at least one filtering parameter concerning the at least one physical appearance characteristic of the at least one genetically-related family member of the user; and
   one or more instructions for selecting at least one health regimen including at least one or more dietary supplements for the user based at least partly on the at least one genetic profile of at least one of the user or the at least one genetically-related family member of the user.

* * * * *